United States Patent
Li et al.

(10) Patent No.: US 11,860,118 B2
(45) Date of Patent: Jan. 2, 2024

(54) GOLD NANOPARTICLE AGGREGATION-INDUCED QUANTITATIVE PHOTOTHERMAL BIOSENSING USING A THERMOMETER

(71) Applicant: Board of Regents, The University of Texas System, Austin, TX (US)

(72) Inventors: XiuJun Li, El Paso, TX (US); Wan Zhou, El Paso, TX (US)

(73) Assignee: BOARD OF REGENTS, THE UNIVERSITY OF TEXAS SYSTEM, Austin, TX (US)

( * ) Notice: Subject to any disclaimer, the term of this patent is extended or adjusted under 35 U.S.C. 154(b) by 608 days.

(21) Appl. No.: 17/112,841

(22) Filed: Dec. 4, 2020

(65) Prior Publication Data
US 2021/0247351 A1 Aug. 12, 2021

Related U.S. Application Data

(60) Provisional application No. 62/944,262, filed on Dec. 5, 2019.

(51) Int. Cl.
*G01N 27/327* (2006.01)
*B82Y 35/00* (2011.01)

(52) U.S. Cl.
CPC ..... *G01N 27/3278* (2013.01); *G01N 27/3276* (2013.01); *G01N 27/3277* (2013.01); *B82Y 35/00* (2013.01)

(58) Field of Classification Search
None
See application file for complete search history.

(56) References Cited

PUBLICATIONS

N. Shokoufi, et al., "Microfluidic chip-photothermal lens microscopy for DNA hybridization assay using gold nanoparticles", Analytical and Bioanalytical Chemistry, 411: p. 6119-6128 + Supplement info., Sep. 1, 2019.*

Liu et al.; "Enzyme-Free Colorimetric Detection of DNA by Using Gold Nanoparticles and Hybridization Chain Reaction Amplification"; Anal Chem.; 2013; 85; pp. 7689-7695.

Deng et al.; "Gold Nanoparticles with Asymmetric Polymerase Chain Reaction for Colorimetric Detection of DNA Sequence"; Anal. Chem.; 2012; 84; pp. 1253-1258.

Zhang et al.; "A redox-activated theranostic nanoagent: toward multi-mode imaging guided chemo-photothermal therapy"; Chem Sci.; Sep. 7, 2018; vol. 9, No. 33; pp. 6749-6757.

Zhan et al.; "The Role of Nanoparticle Design in Determining analytical Performance of Lateral Flow Immunoassays"; Nano Lett.; 2017; 17; pp. 7207-7212.

Ma et al., "Label-Free Detection of Sequence-Specific DNA Based on Fluorescent Silver Nanoclusters-Assisted Surface Plasmon-Enhanced Energy Transfer," ACS Applied Materials and Interfaces, 2015, 7(23), 12856-12863, DOI: 10.1021/acsami.5b03837.

(Continued)

*Primary Examiner* — J. Christopher Ball
(74) *Attorney, Agent, or Firm* — YEE & ASSOCIATES, P.C.

(57) ABSTRACT

A biosensing system configured to detect a target DNA and methods of detecting a target DNS are presented. The biosensing system comprises a biosensor comprising a suspension of a hybridization buffer containing dispersed gold nanoparticles, sodium chloride, and single-stranded DNA probes configured to undergo DNA hybridization with the target DNA.

17 Claims, 15 Drawing Sheets

(56) References Cited

PUBLICATIONS

He et al., "Quenching the Chemiluminescence of Acridinium Ester by Graphene Oxide for Label-Free and Homogeneous DNA Detection," ACS Applied Materials and Interfaces, 2013, 5(21), 11336-11340, DOI: 10.1021/am404138x.

Liu et al., "Detection of *Mycobacterium tuberculosis* Using a Capillary-Array Microsystem with Integrated DNA Extraction, Loop-Mediated Isothermal Amplification, and Fluorescence Detection," Analytical Chemistry, 2013, 85(9), 4698-4704, DOI: 10.1021/ac400412m.

Yu et al., "Tumor Microenvironment-Triggered Fabrication of Gold Nanomachines for Tumor-Specific Photoacoustic Imaging and Photothermal Therapy," Chem. Sci., 2017, 8, 4896-4903.

\* cited by examiner

GOLD NANOPARTICLE AGGREGATION-INDUCED QUANTITATIVE PHOTOTHERMAL BIOSENSING USING A THERMOMETER

CROSS-REFERENCE TO RELATED APPLICATION

This application claims priority to Provisional Application No. 62/944,262, filed on Dec. 5, 2019, the contents of which are incorporated herein by reference in their entirety.

STATEMENT REGARDING FEDERALLY FUNDED RESEARCH

This invention was made with government support from the National Institute of Allergy and Infectious Disease of the NIH (R21AI107415), the U.S. NSF-PREM program (DMR 1827745), and the National Institute of General Medical Sciences of the NIH (SC2GM105584). The government has certain rights in the invention.

BACKGROUND INFORMATION

1. Field

The present disclosure relates generally to biosensing and more specifically to detecting and quantifying DNA using photothermal biosensing.

2. Background

Quantitative and sensitive genetic analysis techniques play a crucial role in numerous fields involved in clinical diagnostics, forensic science, drug development, food safety surveillance, and environmental monitoring. A number of DNA detection methods have been developed including colorimetry, fluorescence, chemiluminescence, and electrochemistry. However, most methods still require bulky and costly instruments.

Among all detection methods, nanomaterial-based colorimetric assays, especially using gold nanoparticles (gold nanoparticles)-based biosensors have been the most commonly used detection method due to the unique surface plasmon resonance (SPR) absorption of gold nanoparticles, simple operation, and distinct color changes. However, most colorimetric methods pose the issue of low detection sensitivity and are not suitable for quantitative detection unless using specialized instruments, such as a microplate reader.

Conventional nucleic acid detection methods mainly consist of nucleic acid amplification-based methods, such as polymerase chain reaction (PCR) and DNA hybridization-based techniques, such as a DNA microarray. These conventional nucleic acid detection methods largely require two functionalization processes: (1) specific functionalization of gold nanoparticles (or some other nanomaterials) mostly with —SH functional groups and (2) functionalization of DNA products primers/probes with other functional groups, such as —NH2, to link with gold nanoparticles, or some fluorescence fluorophores (e.g., fluorescein amidite (FAM), Cy3, Cy5, Cy7, etc.) for the purpose of detection. The functionalization processes make all of the detection methods at least one of undesirably costly, undesirably cumbersome, or undesirably time-consuming.

Moreover, one DNA-functionalized nanosensor is usually limited to one target. Changing to a different target relies on a new round of nanoparticle functionalization. Accordingly, such peculiar recognition, amplification, and detection mechanisms pose limits for versatile broad applications in detecting different DNA sequences. Hence, there has been an increasing interest in the development of a universal platform integrated with label-free and DNA amplification-free biosensing mechanisms for quantitative DNA detection at the point of care.

Photothermal (PT) effect has been extensively studied and applied in cancer therapy because of the unique photothermal conversion property of photothermal agents, involving in gold-based nanomaterials, carbon-based nanomaterials, and organic molecule dyes. Recently, new applications of photothermal agents have been explored, in which nanomaterials-based photothermal biosensing emerged as a novel and attractive method in the quantitative detection of biomolecules.

A photothermal immunoassay platform can be used for the quantitative detection of protein-based cancer biomarkers using an inexpensive thermometer. By introducing different photothermal probes, such as Prussian blue nanoparticles (PB NPs) and small organic molecules (i.e., oxidized 3,3',5,5'-tetramethylbenzidine or oxidized TMB), the target information on disease biomarkers can be converted into photothermal signals (i.e., temperature changes) and, thus quantitatively measured simply by using a household thermometer. As compared to the conventional enzyme-linked immunosorbent assay (ELISA), which is based on colorimetric detection, the photothermal immunoassay is superior as it provides a simple, low-cost, and quantitative detection platform, in which no costly and bulky analytical instrument or trained personnel is needed, with minimal color interference. Unfortunately, most photothermal biosensing platforms target protein-based biomarkers, there are few reports to develop new photothermal biosensing platforms for genetic analysis.

Therefore, it would be desirable to have a method and apparatus that takes into account at least some of the issues discussed above, as well as other possible issues. For example, it would be desirable to develop a photothermal biosensing platform for genetic analysis.

SUMMARY

An embodiment of the present disclosure provides a method of detecting a target DNA. A DNA sample is added to a biosensor comprising a suspension of a hybridization buffer containing dispersed gold nanoparticles, sodium chloride, and single-stranded DNA probes configured to undergo DNA hybridization with the target DNA. A beam of near-infrared radiation is sent into the biosensor by a laser, wherein the beam of near-infrared radiation is configured to induce a photothermal effect in any aggregated gold nanoparticles present in the biosensor. A temperature of the biosensor is detected after sending the beam of near-infrared radiation into the biosensor. Whether the target DNA is present in the DNA sample is determined based on the temperature of the biosensor.

Another embodiment of the present disclosure provides a biosensing system configured to detect a target DNA. The biosensing system comprises a biosensor and a laser. The biosensor comprises a suspension of a hybridization buffer containing dispersed gold nanoparticles, sodium chloride, and single-stranded DNA probes configured to undergo DNA hybridization with the target DNA. The laser is configured to direct a beam of near-infrared radiation into the biosensor, wherein the beam of near-infrared radiation is configured to induce a photothermal effect in any aggregated gold nanoparticles present in the biosensor.

Yet another embodiment of the present disclosure provides a method of detecting a target DNA. A first solution of single-stranded DNA probes in a hybridization buffer is added to a suspension of dispersed gold nanoparticles to form a protected gold nanoparticle suspension, wherein the single-stranded DNA probes are selected to undergo DNA hybridization with the target DNA. A second solution of sodium chloride in the hybridization buffer is added to the protected gold nanoparticle suspension to form a biosensor configured to detect the target DNA.

The features and functions can be achieved independently in various embodiments of the present disclosure or may be combined in yet other embodiments in which further details can be seen with reference to the following description and drawings.

BRIEF DESCRIPTION OF THE DRAWINGS

The novel features believed characteristic of the illustrative embodiments are set forth in the appended claims. The illustrative embodiments, however, as well as a preferred mode of use, further objectives and features thereof, will best be understood by reference to the following detailed description of an illustrative embodiment of the present disclosure when read in conjunction with the accompanying drawings, wherein:

DETAILED DESCRIPTION

The illustrative examples recognize and take into account one or more different considerations. The illustrative examples recognize and take into account that Tuberculosis (TB) caused by the *bacillus Mycobacterium tuberculosis* (MTB) has been one of the deadliest "big 3" infectious diseases resulting in around 1.5 million deaths annually, particularly in low-income countries.

The illustrative examples recognize and take into account that various detection methods targeting MTB DNA have been developed including colorimetry, electrochemistry, fluorescence, and chemiluminescence. However, most of these methods require complicated DNA amplification procedures, sophisticated infrastructure, and well-trained personnel, which significantly lead to the high cost of TB diagnosis and limit their accessibility in low-resource settings. In the illustrative examples, MTB DNA is one of the target DNAs. MTB DNA has been to demonstrate the application of the novel gold nanoparticle aggregation-based photothermal biosensing in genetic analysis using a common thermometer, with no assistance from any DNA amplification process or expensive instruments.

Under optimal conditions, quantitative photothermal biosensing of target DNA could be achieved by simply monitoring the temperature changes of gold nanoparticle suspensions using a thermometer.

The use of the word "a" or "an" when used in conjunction with the term "comprising" in the claims and/or the specification may mean "one," but it is also consistent with the meaning of "one or more," "at least one," and "one or more than one."

The terms "about" or "approximately" are defined as being close to as understood by one of ordinary skill in the art. In one non-limiting embodiment the terms are defined to be within 10%, preferably within 5%, more preferably within 1%, and most preferably within 0.5%.

The term "substantially" and its variations are defined to include ranges within 10%, within 5%, within 1%, or within 0.5%.

The terms "wt. %," "vol. %," or "mol. %" refer to a weight, volume, or molar percentage of a component, respectively, based on the total weight, the total volume, or the total moles of material that includes the component. In a non-limiting example, 10 moles of component in 100 moles of the material is 10 mol. % of component.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

Figure 1:
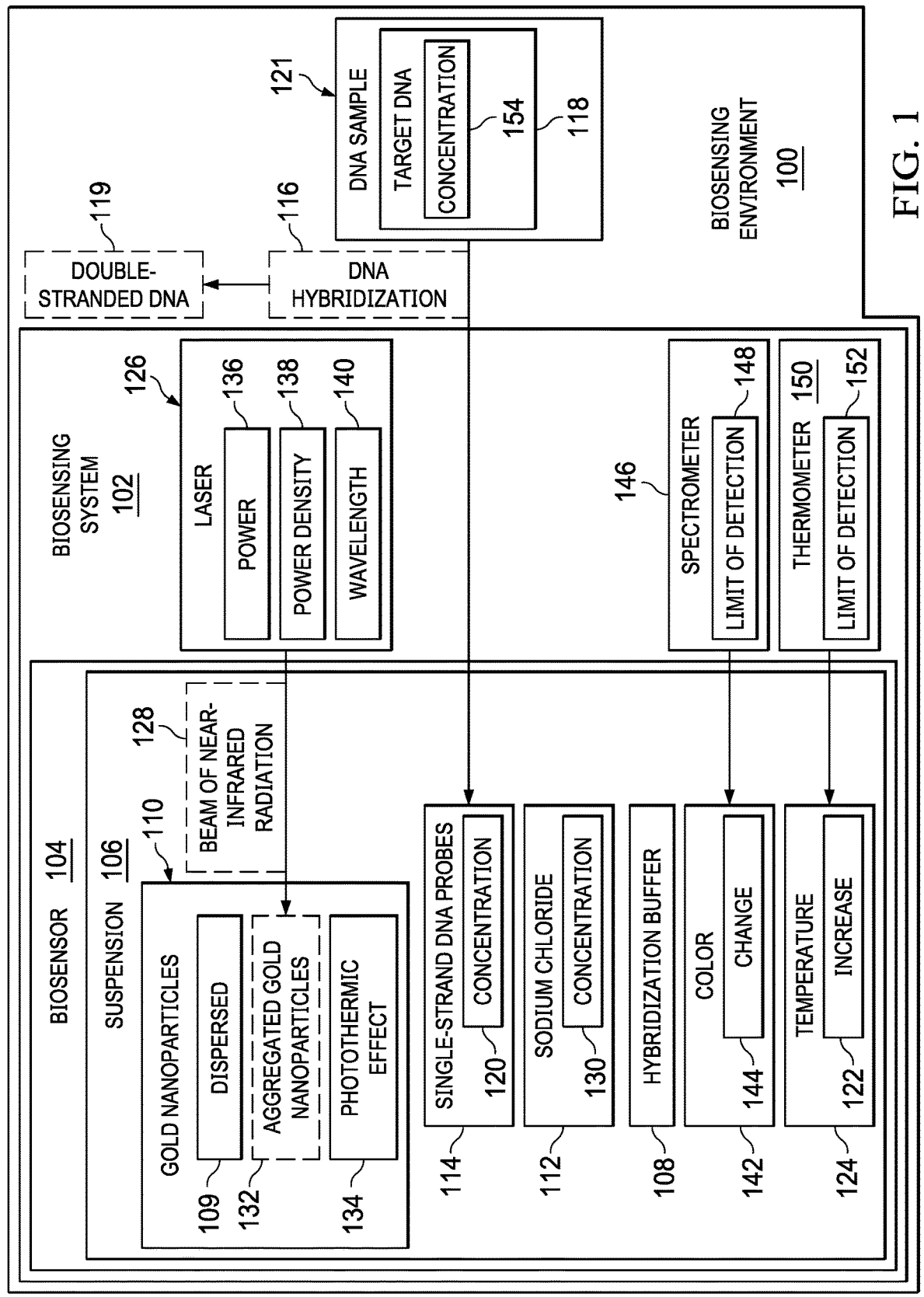
FIG. 1 is an illustration of a block diagram of a biosensing environment in which an illustrative embodiment may be implemented.

Turning now to FIG. 1, an illustration of a block diagram of a biosensing environment is depicted in which an illustrative embodiment may be implemented. Biosensing environment 100 includes biosensing system 102. Biosensing system 102 is configured to detect and quantify target DNA 118. Biosensing system 102 comprises biosensor 104 comprising suspension 106 of hybridization buffer 108 containing dispersed 109 gold nanoparticles 110, sodium chloride 112, and single-stranded DNA probes 114 configured to undergo DNA hybridization 116 with target DNA 118.

Target DNA 118 takes any desirable form. In some illustrative examples, target DNA 118 is the DNA of a bacteria. In some illustrative examples, target DNA 118 is *M. tuberculosis*. In some illustrative examples, target DNA 118 is *B. pertussis*. In some illustrative examples, target DNA 118 is *E. coli*. In some illustrative examples, target DNA 118 is MCF-7 breast cancer cells. In some illustrative examples, target DNA 118 is a genomic DNA sequence extracted from one of *M. tuberculosis* genomic DNA, *B. pertussis*, *E. coli*, breast cancer cells (MCF-7), cancer associated miRNA (miRNA-141), or parasitic infection related *G. lamblia*.

Gold nanoparticles 110 are not functionalized. Gold nanoparticles 110 may be referred to as "bare" or "unmodified". Gold nanoparticles 110 have exposed surfaces of gold. Gold nanoparticles 110 have any desirable diameter. Gold nanoparticles 110 have a diameter selected such that gold nanoparticles 110 will be in suspension. In some illustrative examples, gold nanoparticles 110 have a diameter selected such that gold nanoparticles 110 do not precipitate out of solution. In some illustrative examples, it is desirable for gold nanoparticles 110 to have as large a diameter as possible without gold nanoparticles 110 precipitating out of suspension 106. In some illustrative examples, gold nanoparticles 110 have a diameter in the range of 5 nm to 300 nm. In some illustrative examples, gold nanoparticles 110 have a diameter of 20 nm. In some illustrative examples, the concentration of gold nanoparticles 110 can be from 10 pM to 1 µM.

Single-stranded DNA probes 114 are adsorbed onto dispersed 109 gold nanoparticles 110 via van der Waals attraction. The van der Waals attraction is between the exposed bases of single-stranded DNA probes 114 and the gold surfaces of dispersed 109 gold nanoparticles 110.

Single-stranded DNA probes 114 protect dispersed 109 gold nanoparticles 110 from aggregation induced by sodium chloride 112. Without single-stranded DNA probes 114 in biosensor 104, sodium chloride 112 induces aggregation of dispersed 109 gold nanoparticles 110 into aggregated gold nanoparticles 132. Dispersed 109 gold nanoparticles 110 maintain their dispersed 109 status due to protection by single-stranded DNA probes 114.

Hybridization buffer 108 is selected to provide an environment for DNA hybridization 116 of single-stranded DNA probes 114 with target DNA 118 upon introduction of target DNA 118. When target DNA 118 is introduced into biosensor 104, target DNA 118 and single—stranded DNA probes 114 undergo DNA hybridization 116 to form double-stranded DNA 119. When single-stranded DNA probes 114 undergo DNA hybridization 116, single-stranded DNA probes 114 no longer protect gold nanoparticles 110 from aggregation.

There is a disparity in adsorption onto gold nanoparticles 110 between single-stranded DNA probes 114 and double-stranded DNA, such as double-stranded DNA 119. Specifically, single-stranded DNA probes 114 are able to be adsorbed onto gold nanoparticles 110 via van der Waals attraction between the exposed bases and the gold surface. Double-stranded DNAs, such as double-stranded DNA 119, have little affinity to gold nanoparticles 110. Double-stranded DNA 119 has a stable double-helix geometry that inhibits the exposure of nucleobases and leads to the electrostatic repulsive interaction between gold nanoparticles 110 and the negatively charged phosphate backbone of double-stranded DNA 119.

Concentration 120 of single-stranded DNA probes 114 in biosensor 104 is sufficient to protect dispersed 109 gold nanoparticles 110 from aggregation induced by sodium chloride 112. Concentration 120 of single-stranded DNA probes 114 is selected such that suspension 106 has absorbance and temperature changes substantially similar to a suspension of only gold nanoparticles 110 in hybridization buffer 108. In some illustrative examples, concentration 120 of single-stranded DNA probes 114 is selected such that substantially all single-stranded DNA probes 114 are adsorbed to gold nanoparticles 110. In some illustrative examples, concentration 120 of single-stranded DNA probes 114 is selected such that few, if any, of single-stranded DNA probes 114 are free in suspension 106. In some illustrative examples, concentration 120 of single-stranded DNA probes 114 is 160 nanoMolar.

Figure 12:
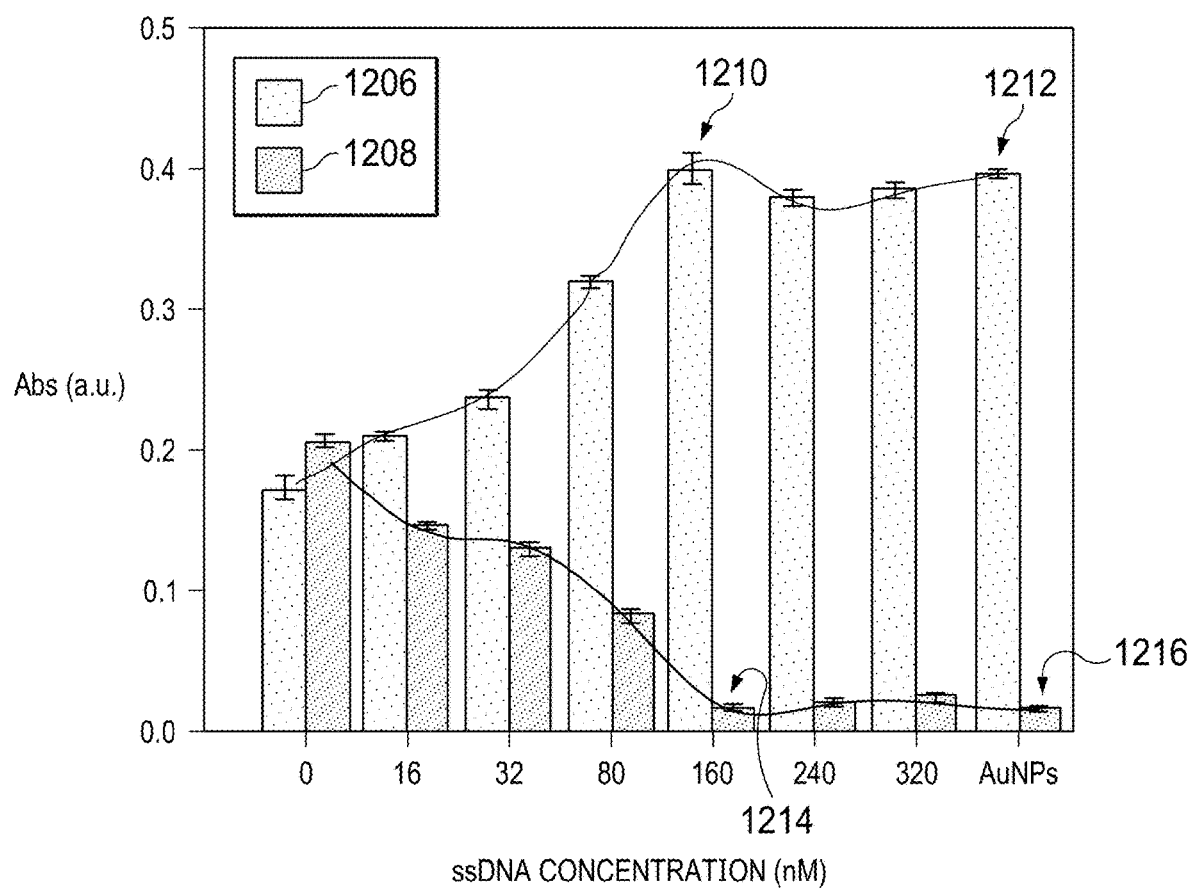
FIG. 12 is an illustration of a bar graph of absorbances at 520 and 800 nm for suspensions having different concentrations of single-stranded DNA concentrations in the gold nanoparticle aggregation-based photothermal biosensing method in accordance with an illustrative embodiment.
Figure 13:
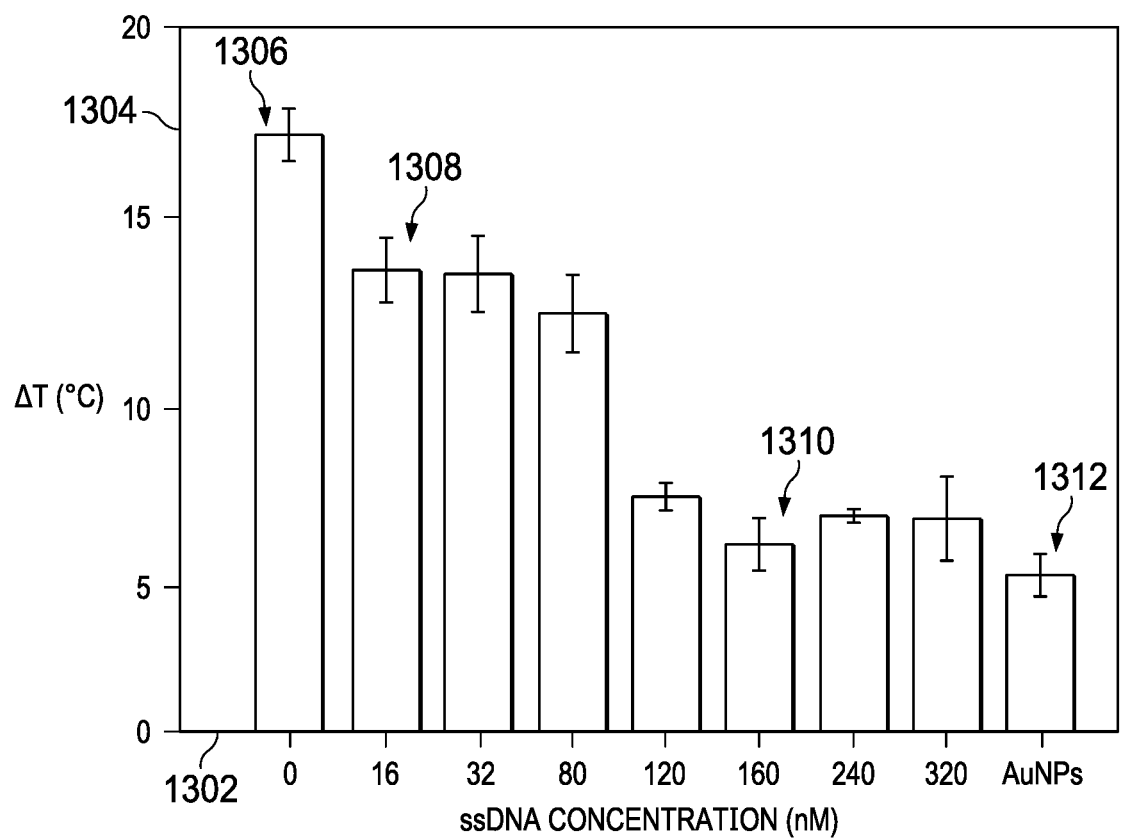
FIG. 13 is an illustration of a bar graph of temperature increases of suspensions having different single-stranded DNA concentrations in the gold nanoparticle aggregation-based photothermal biosensing method under the 808 nm laser irradiation in accordance with an illustrative embodiment.

In some illustrative examples, biosensor 104 comprises concentration 120 of single-stranded DNA probes 114 configured to interact with dispersed 109 gold nanoparticles 110. In some illustrative examples, biosensor 104 comprises concentration 120 of single-stranded DNA probes 114 configured to provide an absorbance at 520 nm equivalent to an absorbance at 520 nm of a suspension of dispersed 109 gold nanoparticles 110. In some illustrative examples, biosensor 104 comprises concentration 120 of single-stranded DNA probes 114 configured to provide biosensor 104 with temperature 124 increase 122 in response to beam of near-infrared radiation 128 equivalent to a temperature increase in response to a beam of near-infrared radiation of a suspension of dispersed 109 gold nanoparticles 110. FIGS. 12 and 13 provide a description of selecting concentration 120 of single-stranded DNA probes 114 for biosensor 104.

Analysis of DNA sample 121 using biosensing system 102 is based on increase 122 in temperature 124 of biosensor 104 when subjected to irradiation by laser 126. After introduction of DNA sample 121 to biosensor 104, laser 126 sends beam of near-infrared radiation 128 into biosensor 104. Photothermic effect 134 converts the light energy of beam of near-infrared radiation 128 into heat energy.

A difference in photothermic effect 134 exists between gold nanoparticles 110 in different statuses. Dispersed 109 gold nanoparticles 110 have a weak photothermic effect 134 under the irradiation of a near-infrared (NIR) laser, laser 126. Increase 122 in temperature 124 is minimal when suspension 106 with dispersed 109 gold nanoparticles 110 is under the irradiation of a near-infrared (NIR) laser, laser 126.

Aggregated gold nanoparticles 132 have a much stronger photothermic effect 134. The aggregation of gold nanoparticles 110 is mainly due to the adsorption disparity onto gold nanoparticles 110 between single-stranded DNA and double-stranded DNA (dsDNA) under the presence of sodium chloride 112. When target DNA 118 is introduced to biosensor 104, target DNA 118 undergoes DNA hybridization 116 with single-stranded DNA probes 114. When single-stranded DNA probes 114 undergo DNA hybridization 116 with target DNA 118, protection of the single-stranded DNA probes 114 is removed. When single-stranded DNA probes 114 undergo DNA hybridization 116 with target DNA 118, sodium chloride 112 is able to access those of gold nanoparticles 110 that are no longer protected. Following DNA hybridization 116, at least some of gold nanoparticles 110 aggregate upon exposure to sodium chloride 112 to form aggregated gold nanoparticles 132.

The quantity of gold nanoparticles 110 that aggregate to form aggregated gold nanoparticles 132 is related to the quantity of single-stranded DNA probes 114 that undergo DNA hybridization 116. The quantity of single-stranded DNA probes 114 that undergo DNA hybridization 116 is related to the concentration 154 of target DNA 118 that is introduced to biosensor 104.

Increase 122 in temperature 124 is related to the quantity of gold nanoparticles 110 that undergo aggregation to form aggregated gold nanoparticles 132. Increase 122 in temperature 124 is thus related to the concentration 154 of target DNA 118 introduced to biosensor 104.

Using biosensor 104, the presence and the concentration of target DNA 118 introduced to biosensor 104 is detected using increase 122 in temperature 124. There is a direct relationship between increase 122 in temperature 124 and concentration 154 of target DNA 118. In some illustrative examples, there is a logarithmic relationship between increase 122 of temperature 124 with the logarithm of concentration 154 of target DNA 118.

Figure 8:
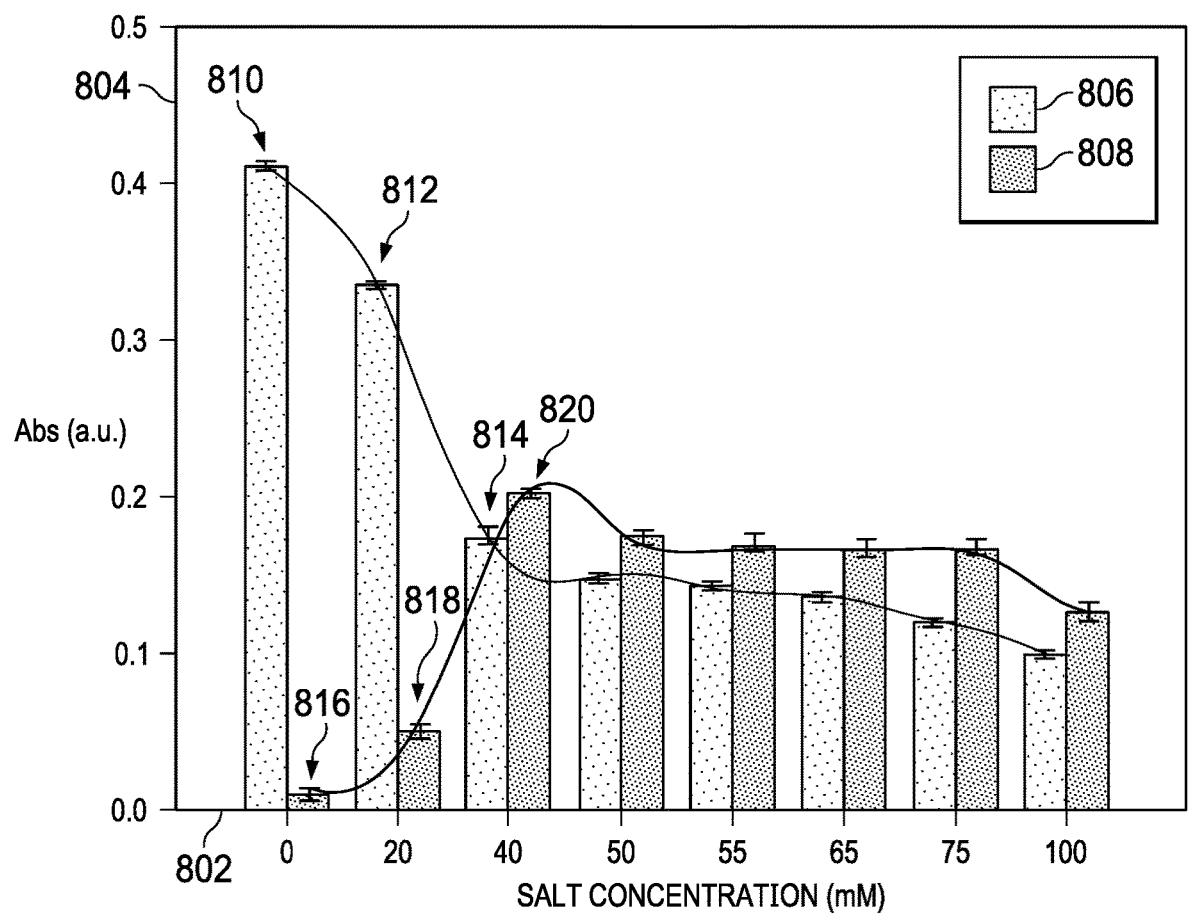
FIG. 8 is an illustration of a bar graph of absorbances at 520 and 800 nm for suspensions having different sodium chloride concentrations in the gold nanoparticle aggregation-induced photothermal biosensing method in accordance with an illustrative embodiment.
Figure 9:
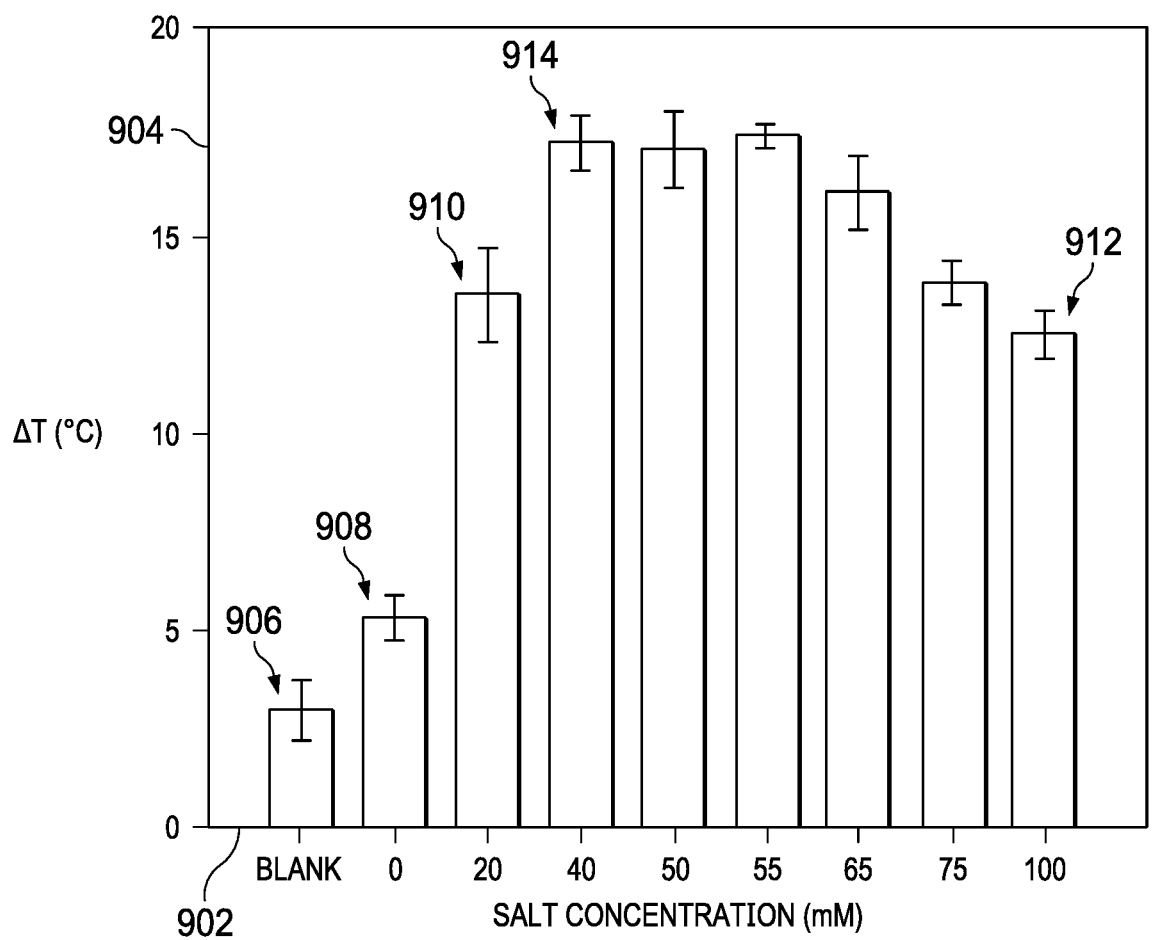
FIG. 9 is an illustration of a bar graph of temperature increases of suspensions having different sodium chloride concentrations in the gold nanoparticle aggregation-induced photothermal biosensing method under 808 nm laser irradiation in accordance with an illustrative embodiment.

Sodium chloride 112 has concentration 130 in biosensor 104. Concentration 130 is selected to trigger aggregation of gold nanoparticles 110 without causing gold nanoparticles 110 to precipitate out of solution. In some illustrative examples, biosensor 104 comprises concentration 130 of sodium chloride 112 configured to produce a maximum temperature increase due to gold nanoparticle aggregation. In some illustrative examples, biosensor 104 comprises concentration 130 of sodium chloride 112 configured to produce a large temperature increase due to gold nanoparticle aggregation without triggering precipitation of aggregated gold nanoparticles 132. FIGS. 8 and 9 provide a description of selecting concentration 130 of sodium chloride 112 for biosensor 104. In some illustrative examples, sodium chloride 112 has concentration 130 of 40 milliMolar. Concentration 130 of sodium chloride 112 is selected prior to selecting concentration 120 of single-stranded DNA probes 114.

Laser 126 is configured to direct beam of near-infrared radiation 128 into biosensor 104. Beam of near-infrared radiation 128 is configured to induce photothermal effect 134 in any aggregated gold nanoparticles 132 present in biosensor 104. Laser 126 has power 136, power density 138, and wavelength 140. Laser 126 can have power 136 in any desirable range to initiate photothermic effect 134 in gold nanoparticles 110.

Laser 126 has power density 138 sufficient to initiate photothermic effect 134 in gold nanoparticles 110. In some illustrative examples, laser 126 has power density 138 of 5.2 W/cm$^2$. Power density 138 is desirably substantially the same throughout biosensor 104.

Laser 126 is configured to provide beam of near-infrared radiation 128 having wavelength 140 configured to excite gold nanoparticles 110 and initiate photothermic effect 134. In some illustrative examples, wavelength 140 is in the near-infrared range. The near-infrared range includes wavelengths in the range of 700 nm-1400 nm. In some illustrative examples, wavelength 140 is 808 nm.

Other aspects of laser 126 that may be taken into consideration when choosing laser 126 include portability, commercial availability, cost, use without specialized training, and laser regulations. Taking into account any of these aspects of laser 126 may provide this biosensing method as part of point-of-care testing (POCT).

Aggregation of gold nanoparticles 110 to form aggregated gold nanoparticles 132 results in change 144 in color 142 of suspension 106 of biosensor 104. Spectrometer 146 can be used to perform colorimetric detection of change 144 of color 142. However, limit of detection 148 of spectrometer 146 is undesirable. It is desirable to have a higher sensitivity than provided by spectrometer 146. It is desirable to have a lower limit of detection than limit of detection 148 provided by spectrometer 146. In one illustrative example, limit of detection 148 was calculated based on three folds standard deviation above the blank (hybridization buffer 108) and determined to be 2.0 nM. Additionally, spectrometer 146 may be at least one of undesirably costly, undesirably bulky, and using trained personnel.

Change 144 in color 142 is due to aggregation of gold nanoparticles 110 to form aggregated gold nanoparticles 132. Increase 122 in temperature 124 is also due to presence of aggregated gold nanoparticles 132. Thus, biosensor 104 can be used to detect target DNA 118 using DNA hybridization 116 to form aggregated gold nanoparticles 132.

Increase 122 in temperature 124 is measured after biosensor is irradiated by laser 126 for a selected time. In some illustrative examples, irradiation using a near-infrared (NIR) laser, laser 126, is performed until a heat balance is achieved. A heat balance is achieved at a plateau in increase 122 in temperature 124. The heat balance is achieved between heat generation from photothermal effect 134 and heat dissipation to the environment. In some illustrative examples, the irradiation time is selected to acquire a stable and sensitive temperature measurement. In some illustrative examples, a laser irradiation time of between 5 minutes and 10 minutes is selected as the irradiation time for biosensing using biosensor 104. In some illustrative examples, a laser irradiation time of 8 minutes is selected as the irradiation time for biosensing using biosensor 104.

Thermometer 150 is configured to detect temperature changes of suspension 106. Thermometer 150 is used to detect increase 122 in temperature 124. Although thermometer 150 can be a low-cost thermometer, high sensitivity can be achieved with the low-cost thermometer. Thermometer 150 can have a greater sensitivity than spectrometer 146. For example, thermometer 150 can have limit of detection 152 as low as 0.28 nM, about 10-fold lower than limit of detection 148 in the colorimetric detection method using spectrometer 146.

Photothermal biosensing using thermometer 150 in biosensing system 102 provides improvements over colorimetric detection utilizing spectrometer 146. Compared to change 144 in color 142 observed by the naked eye, photothermal biosensing based on target DNA 118 induced aggregation of gold nanoparticles 110 provides a simple yet reliable platform for the quantitative detection of target DNA 118. Most colorimetric methods pose the issue of low detection sensitivity and are not suitable for quantitative detection unless using specialized instruments, such as spectrometer 146.

Photothermal biosensing using biosensor 104 and thermometer 150 in biosensing system 102 is a low-cost and universal biosensing process. Biosensor 104 is referred to as universal due to the use of bare gold nanoparticles 110 without functionalization.

The use of bare gold nanoparticles 110 allows for biosensor 104 to be easily modified for detecting different types of target DNA 118. To change target DNA 118 detected by biosensor 104, gold nanoparticles 110 can be used with a different set of single-stranded DNA probes configured to hybridize with the new target DNA.

Single-stranded DNA probes 114 are configured to undergo DNA hybridization 116 with target DNA 118. Single-stranded DNA probes 114 will not undergo DNA hybridization without exposure to target DNA 118.

The specificity of biosensor 104 has been confirmed. In one illustrative example, target DNA 118 is M. tuberculosis genomic DNA. In one illustrative example, various nucleic acids including genomic DNA sequences extracted from B. pertussis, E. coli, and breast cancer cells (MCF-7), cancer associated miRNA (miRNA-141), and parasitic infections related G. lamblia DNA, were presented in different DNA samples at 3-fold higher concentrations as interfering substances than target DNA 118 in DNA sample 121 introduced to biosensor 104. UV-vis characterization using absorbances at 650 nm and photothermal biosensing using temperature as readouts were performed on each sample introduced to a biosensor. Only upon the addition of target DNA 118 does an obvious absorbance at 650 nm appear with a dramatic temperature increase of ~9° C. Other samples with the addition of ssDNA, B. pertussis, E. coli, and MCF-7 cells extracted genomic DNA, miRNA-141, and G. lamblia DNA had no apparent temperature change as compared to hybridization buffer 108 as blank. The temperature increase for each of ssDNA, B. pertussis, E. coli, and MCF-7 cells extracted genomic DNA, miRNA-141, and G. lamblia DNA samples were less than 50% of the temperature increase of DNA sample 121 with target DNA 118. More than 200% higher temperature increases were still obtained when detecting target DNA 118 at a 3-fold lower concentration compared to other nucleic acids. The results demonstrated high specificity of biosensor 104 in biosensing system 102 for quantitative genetic analysis even in the presence of higher concentrations of interfering substances. Although specificity is described as being confirmed using M. tuberculosis genomic DNA as target DNA 118, any desirable DNA can be detected. In some illustrative examples, target DNA 118 is B. pertussis. In some illustrative examples, target DNA 118 is E. coli. Target DNA 118 can be any desirable DNA for detection.

Biosensing system 102 was tested using three pairs of respective single-stranded DNA probes and their complementary targets. For each biosensor, the optimal procedures for determining irradiation time, sodium chloride 112 concentration 130, and single-stranded DNA probes 114 concentration 120. Biosensing system 102 has been tested using N. meningitidis, miRNA-141, and G. lamblia as target DNA 118. A distinctive increase 122 (>10° C.) in temperature 124 was obtained in all three targets, compared with the blank of hybridization buffer 108, indicating wide application of biosensing system 102 as a universal photothermal biosensing platform.

Biosensor 104 is referred to as universal due to the ability to modify biosensor 104 to detect any desirable target. The use of bare gold nanoparticles 110 without functionalization allows for biosensor 104 to be easily modified for detecting different types of target DNA 118. To change target detected by biosensor 104, gold nanoparticles 110 can be used with a different set of single-stranded DNA probes configured to hybridize with the new target.

The illustration of biosensing system 102 in FIG. 1 is not meant to imply physical or architectural limitations to the manner in which an illustrative embodiment may be implemented. Other components in addition to or in place of the ones illustrated may be used. Some components may be unnecessary. Also, the blocks are presented to illustrate some functional components. One or more of these blocks may be combined, divided, or combined and divided into different blocks when implemented in an illustrative embodiment.

For example, although spectrometer 146 is displayed, spectrometer 146 may not be present in biosensing system 102. In some illustrative examples, spectrometer 146 is only utilized when testing DNA hybridization 116 of single-stranded DNA probes 114. In some illustrative examples, spectrometer 146 is not present in biosensing system 102 in point-of-care biosensing applications.

As another example, although biosensor 104 is described as configured to detect target DNA 118, biosensor 104 can be utilized to quantitatively detect a wide range of biochemicals and biological organisms, not solely nucleic acids. In some illustrative examples, biosensor 104 can use DNA-based aptamers to detect a variety of different chemicals. In some illustrative examples, biosensor 104 can use DNA-based aptamers to detect at least one of protein biomarkers, microorganisms, cancer cells, or metal ions.

Figure 2:
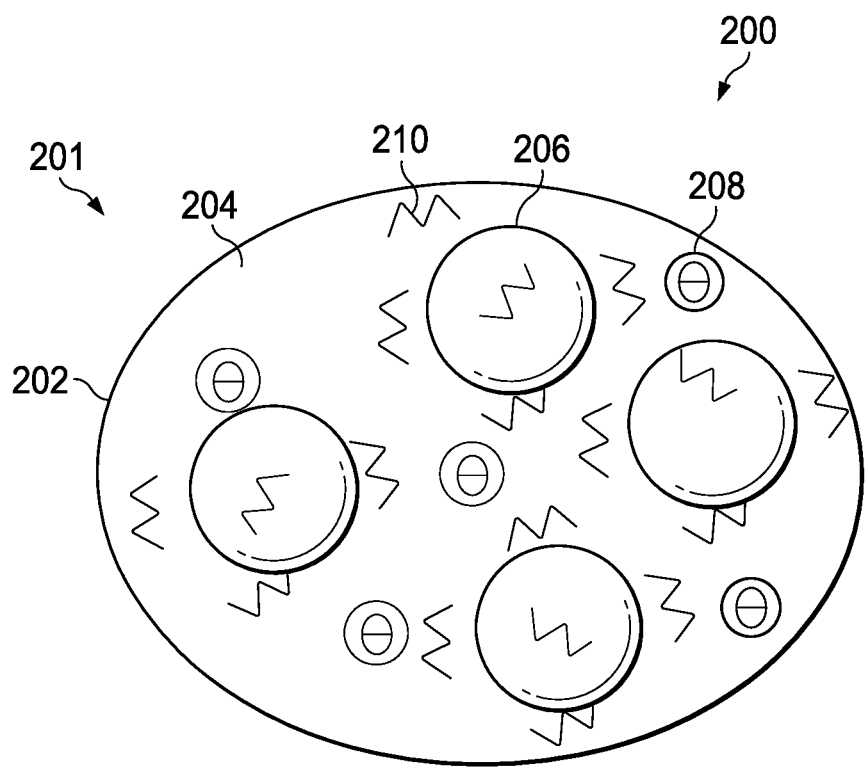
FIG. 2 is an illustration of a biosensor in accordance with an illustrative embodiment.

Turning now to FIG. 2, an illustration of a biosensor is depicted in accordance with an illustrative embodiment. View 200 depicts biosensor 201. Biosensor 201 is a physical implementation of biosensor 104 of FIG. 1. In view 200 of biosensor 201, a DNA sample to be tested has not been added to biosensor 201.

Biosensor 201 comprises suspension 202 of hybridization buffer 204 containing dispersed gold nanoparticles 206, sodium chloride 208, and single-stranded DNA probes 210 configured to undergo DNA hybridization with the target DNA. Hybridization buffer 204 is selected to provide an environment for hybridization of single-stranded DNA probes 210 with a target DNA upon introduction of the target DNA.

Single-stranded DNA probes 210 are adsorbed onto dispersed gold nanoparticles 206 via van der Waals attraction. The van der Waals attraction is between the exposed bases of single-stranded DNA probes 210 and the gold surfaces of dispersed gold nanoparticles 206. Single-stranded DNA probes 210 protect dispersed gold nanoparticles 206 from aggregation induced by sodium chloride 208. Dispersed gold nanoparticles 206 maintain their dispersed status due to protection by single-stranded DNA probes 210. Dispersed gold nanoparticles 206 have a weak photothermal effect under the irradiation of a near-infrared (NIR) laser.

Figure 3:
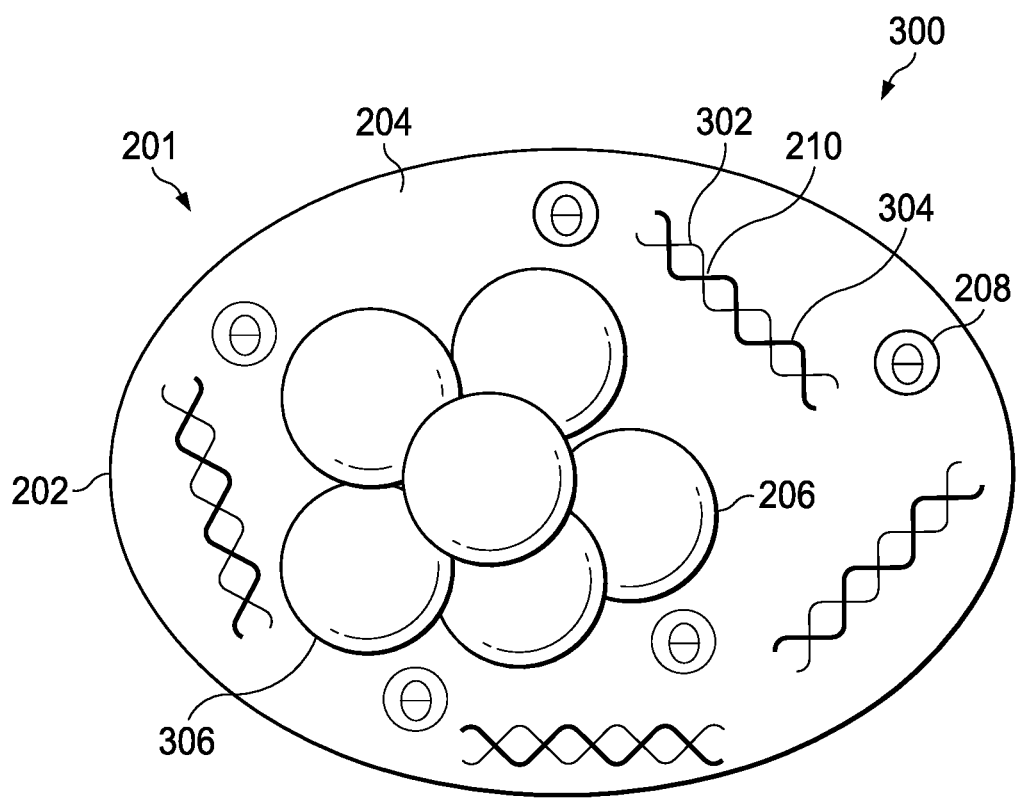
FIG. 3 is an illustration of a biosensor with a DNA sample added that includes a target DNA in accordance with an illustrative embodiment.

Turning now to FIG. 3, an illustration of a biosensor with a DNA sample added that includes a target DNA is depicted in accordance with an illustrative embodiment. In view 300 of biosensor 201, a DNA sample has been added to biosensor 201. The DNA sample included target DNA 302. Target DNA 302 and Single-stranded DNA probes 210 underwent DNA hybridization to form double-stranded DNA 304.

In view 300 of biosensor 201, gold nanoparticles 206 are no longer dispersed. Dispersed gold nanoparticles 206 of FIG. 2 have aggregated to form aggregated gold nanoparticles 306 in view 300. The aggregation of gold nanoparticles 206 is mainly due to the adsorption disparity between single-stranded DNA and double-stranded DNA (dsDNA). An adsorption disparity exists between single-stranded DNA probes 210 of FIG. 2 and double-stranded DNA 304.

Double-stranded DNA, such as double-stranded DNA 304, has little affinity to gold nanoparticles 206 because of the stable double-helix geometry of double-stranded DNA 304. The double-helix geometry inhibits the exposure of nucleobases and leads to the electrostatic repulsive interaction between the negatively charged phosphate backbone and gold nanoparticles 206.

In the presence of target DNA 302, the protection of gold nanoparticles 206 is damaged due to DNA hybridization. Damaging the protection of gold nanoparticles 206 causes the aggregation of gold nanoparticles 206 upon the exposure to sodium chloride 208. Aggregated gold nanoparticles 306 is formed and used as a photothermal agent for photothermal biosensing. As such, an obvious temperature increase can be obtained from biosensor 201 with aggregated gold nanoparticles 306 while being irradiated by the NIR laser.

Figure 4:
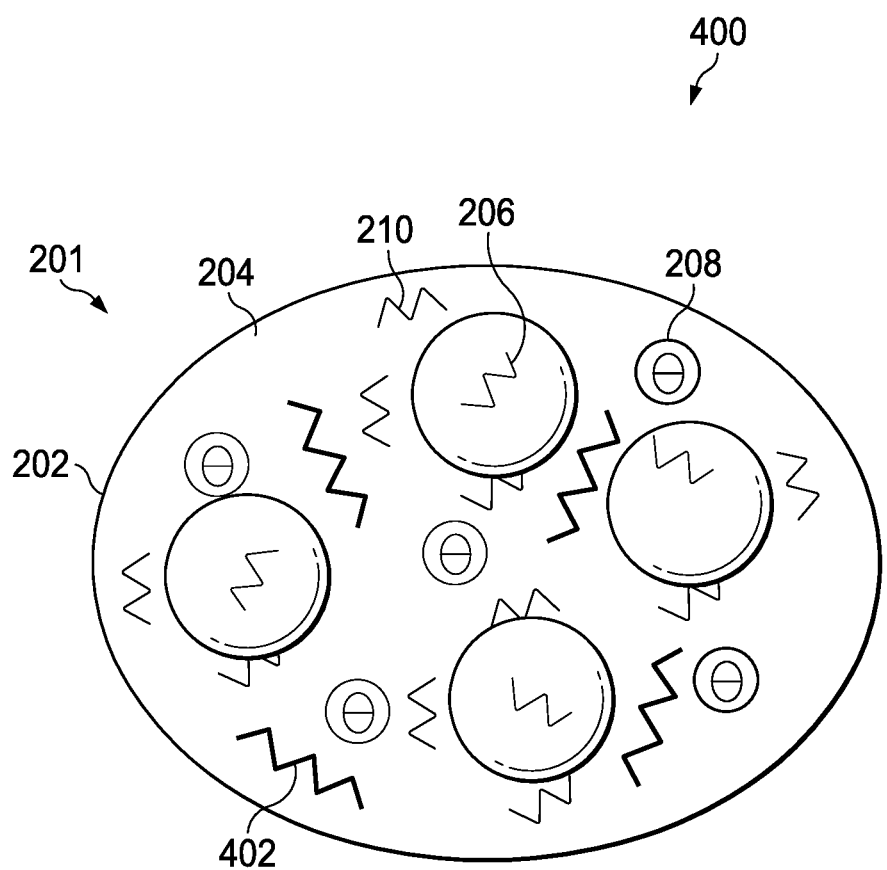
FIG. 4 is an illustration of a biosensor with a DNA sample added that does not includes a target DNA in accordance with an illustrative embodiment.

Turning now to FIG. 4, an illustration of a biosensor with a DNA sample added that does not include a target DNA is depicted in accordance with an illustrative embodiment. In view 400 of biosensor 201, DNA sample 402 has been added to biosensor 201. DNA sample 402 does not include target DNA 302 of FIG. 3. Single-stranded DNA probes 210 are configured to undergo DNA hybridization with target DNA 302. Single-stranded DNA probes 210 will not undergo DNA hybridization without exposure to target DNA 302. Single-stranded DNA probes 210 will not undergo DNA hybridization with DNA sample 402.

Gold nanoparticles 206 remain in dispersed state while adding DNA sample 402 that does not include target DNA 302. Gold nanoparticles 206 in dispersed state cause a negligible temperature increase due to a weak PT effect. As such, a temperature change of biosensor 201 with gold nanoparticles 206 in dispersed state would be minimal while being irradiated by near infrared radiation from a laser.

Detection of target DNA 302 can be achieved by recording the temperature change of biosensor 201 while being irradiated by near infrared radiation from a laser. By recording the temperature change of biosensor 201 while being irradiated by near infrared radiation, target DNA 302 can be detected by using a thermometer. For example, using a thermometer, the temperature change of biosensor 201 depicted in FIG. 3 would be sufficient to indicate the presence of target DNA 302. As another example, using a thermometer, the temperature change of biosensor 201 depicted in FIG. 4 is insufficient to indicate the presence of target DNA 302.

Figure 5:
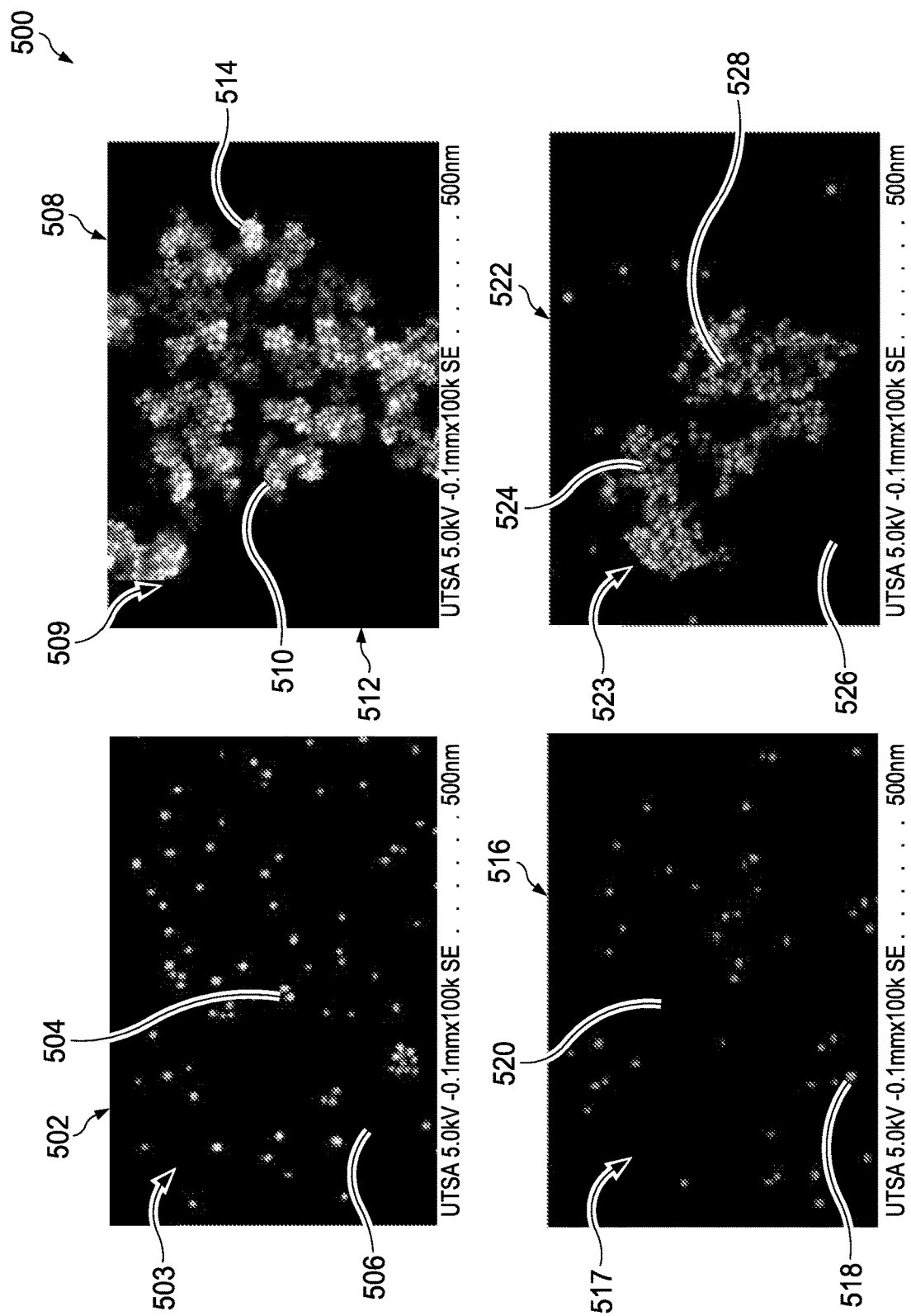
FIG. 5 is an illustration of scanning electron microscopy (SEM) images of different suspensions comprising gold nanoparticles in accordance with an illustrative embodiment.

Turning now to FIG. 5, an illustration of scanning electron microscopy (SEM) images of different suspensions comprising gold nanoparticles is depicted in accordance with an illustrative embodiment. View 500 includes scanning electron microscope (SEM) images of four suspensions comprising gold nanoparticles. SEM image 502 is of gold nanoparticle suspension 503. SEM image 502 is of gold nanoparticles 504 suspended in hybridization buffer 506. Gold nanoparticles 504 are in a dispersed state in hybridization buffer 506. Under laser irradiation, no obvious temperature increase is obtained for gold nanoparticle suspension 503.

SEM image 508 is of suspension 509 comprising gold nanoparticles 510, sodium chloride (not visible), and hybridization buffer 512. The sodium chloride induces aggregation of gold nanoparticles 510 to form aggregated gold nanoparticles 514. The addition of sodium chloride results in a change of the color of gold nanoparticles 510. The color of gold nanoparticles 510 is changed to blue due to gold nanoparticle aggregation. In addition, an obvious temperature increase is obtained under laser irradiation of suspension 509. In this illustrative example, a temperature increase of about 13 degrees Celsius was obtained under laser irradiation.

SEM image 516 is of suspension 517 comprising gold nanoparticles 518, sodium chloride (not visible), single-stranded DNA (not visible), and hybridization buffer 520. In suspension 517, the presence of single-stranded DNA probes maintains gold nanoparticles 518 in a dispersed state. The adsorption of single-stranded DNA probes on the surface of gold nanoparticles 518 protects gold nanoparticles 518 from aggregation due to the presence of sodium chloride. As gold nanoparticles 518 are protected from aggregation by the single-stranded DNA probes, suspension 517 has no obvious changes are observed in UV-vis spectra, SEM image 516, and temperature measurement when compared to suspension 503.

SEM image 522 is of suspension 523 comprising gold nanoparticles 524, sodium chloride (not visible), single-stranded DNA (not visible), hybridization buffer 526, and a DNA sample (not visible). Suspension 523 is the same as suspension 517 with a DNA sample introduced.

In suspension 523, the single-stranded DNA probes are no longer protecting gold nanoparticles 518 from aggregation. In suspension 523, the sodium chloride has induced aggregation of gold nanoparticles 524 to form aggregated gold nanoparticles 528.

In the presence of the DNA sample, aggregation of gold nanoparticles 524 has occurred to form aggregated gold nanoparticles 528. Thus, the DNA sample includes the target DNA. Upon introduction of the DNA sample, the hybridization of the single-stranded DNA probes and the target DNA left gold nanoparticles 524 unprotected from the sodium chloride. After DNA hybridization of the DNA sample and the single-stranded DNA probes, the gold nanoparticles 524 are aggregated by the sodium chloride.

The color of suspension 523 changed from red to purple/blue and a shoulder peak centered at around 650 nm appeared. The color change of suspension 523 was primarily due to DNA hybridization and gold nanoparticle aggregation. An obvious temperature increase was recorded in suspension 523 under laser irradiation. In this illustrative example, the temperature change was ~11° C.

As evidenced by the substantially similar UV-vis spectra, SEM image, and temperature measurement for suspension 509 and suspension 523, biosensing of the DNA sample can be performed using a suspension including single-stranded DNA probes configured to undergo DNA hybridization with the target DNA. A temperature change occurs upon radiating suspension 517 in the presence of the target DNA. Temperature signals of biosensors including gold nanoparticles, sodium chloride, and single-stranded DNA probes be used as readouts for biosensing. Target DNA-induced gold nanoparticle aggregation can be used for the photothermal biosensing using a thermometer.

Figure 6:
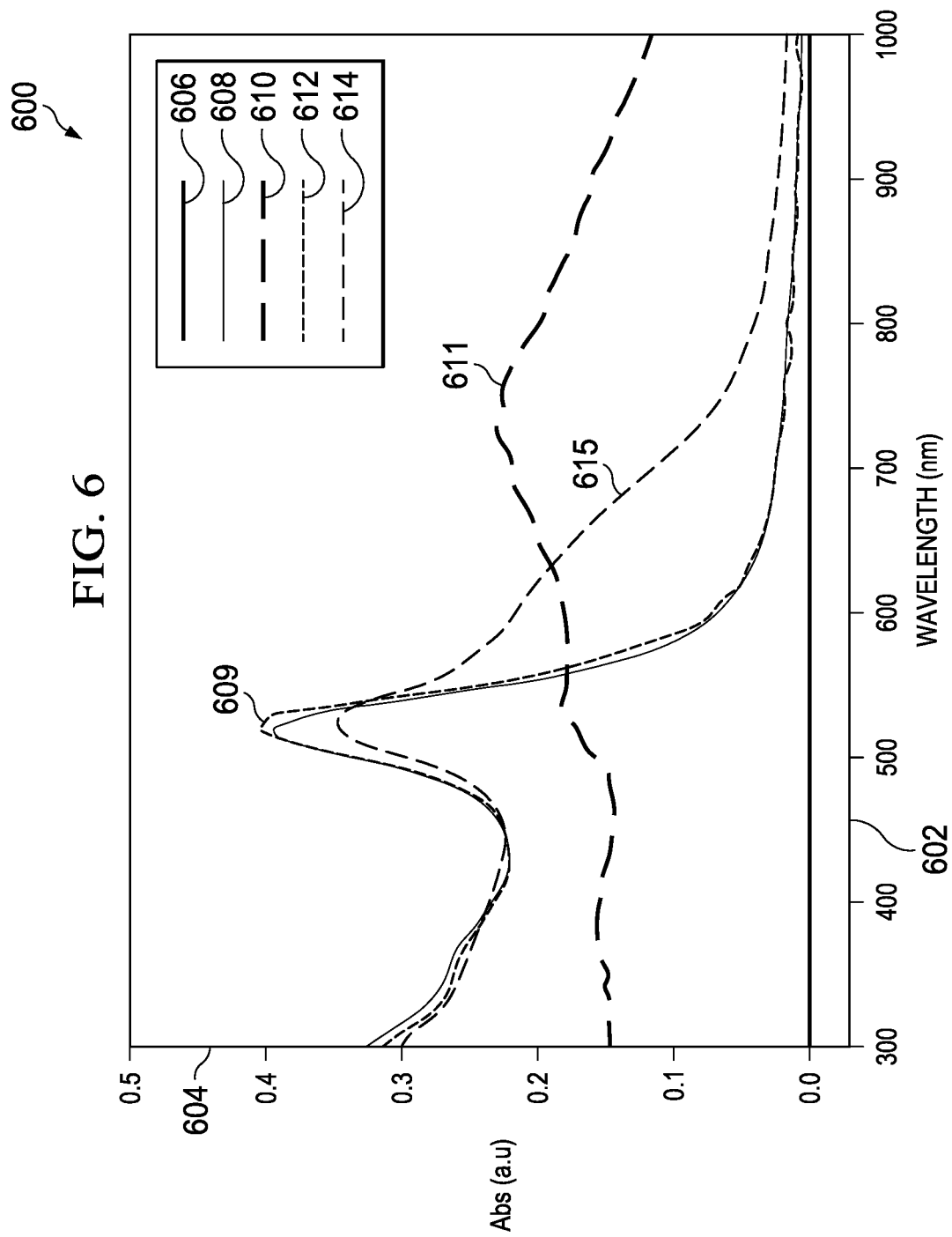
FIG. 6 is an illustration of a line graph of UV-vis spectra of different suspensions comprising gold nanoparticles in accordance with an illustrative embodiment.

Turning now to FIG. 6, an illustration of a line graph of UV-vis spectra of different suspensions comprising gold nanoparticles is depicted in accordance with an illustrative embodiment. Line graph 600 displays the UV-vis spectra of the suspensions of FIG. 5. Line graph 600 includes x-axis 602 of wavelength in nanometers and y-axis 604 of absorbance in absorbance units. Line 606 is of a suspension of only the hybridization buffer. Line 608 is of a suspension of the hybridization buffer and gold nanoparticles. Line 608 displays absorbance data of suspension 503 of FIG. 5. Line 608 includes absorption peak 609 at 520 nm.

Line 610 is of a suspension of the hybridization buffer, gold nanoparticles, and sodium chloride. In this illustrative example, the sodium chloride provided was 40 mM (milli-Molar). Line 610 displays absorbance data of suspension 509 of FIG. 5. Line 610 displays peak 611 at 750 nm due to red shift of the SPR peak, which resulted from aggregation of the gold nanoparticles.

Line 612 is of a suspension of the hybridization buffer, gold nanoparticles, sodium chloride, and single-stranded DNA probes. Line 612 displays absorbance data of suspension 517 of FIG. 5.

Line 614 is of a suspension of the hybridization buffer, gold nanoparticles, sodium chloride, single-stranded DNA probes, and DNA sample including the target DNA. In this illustrative example, the sodium chloride provided was 40 mM and the target DNA had a concentration of 1600 nM. Line 614 displays absorbance data of suspension 523 of FIG. 5. The color of suspension 523 changed from red to purple/blue. As can be seen in line graph 600, shoulder peak 615 centered at around 650 nm appeared in line 614, which was mainly due to DNA hybridization and gold nanoparticle aggregation.

As evidenced in FIGS. 5 and 6, the biosensing system can be used to detect a target DNA using temperature detection. In this photothermal biosensing system, different factors can significantly affect the detection performance, such as concentrations of sodium chloride, concentrations of single-stranded DNA probes, and laser irradiation time. Therefore, the factors should be selected to provide desirable levels of detection of the target DNA.

Figure 7:
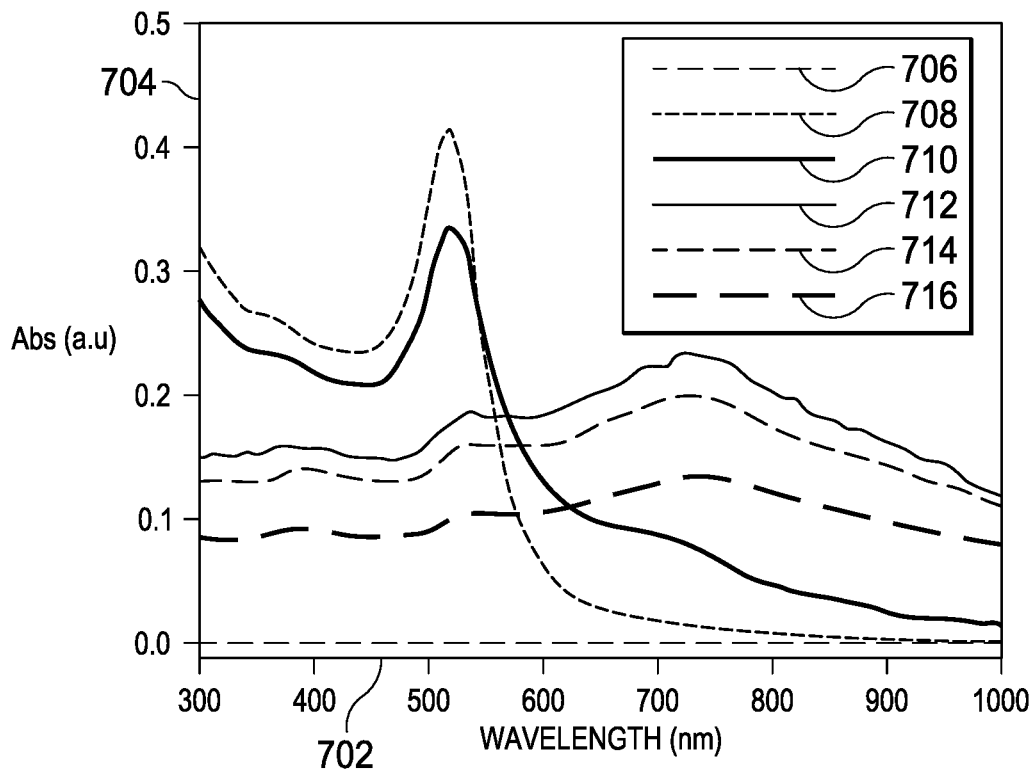
FIG. 7 is an illustration of a line graph of the UV-vis spectra of suspensions having different sodium chloride concentrations in the gold nanoparticle aggregation-induced photothermal biosensing method in accordance with an illustrative embodiment.
Figure 10:
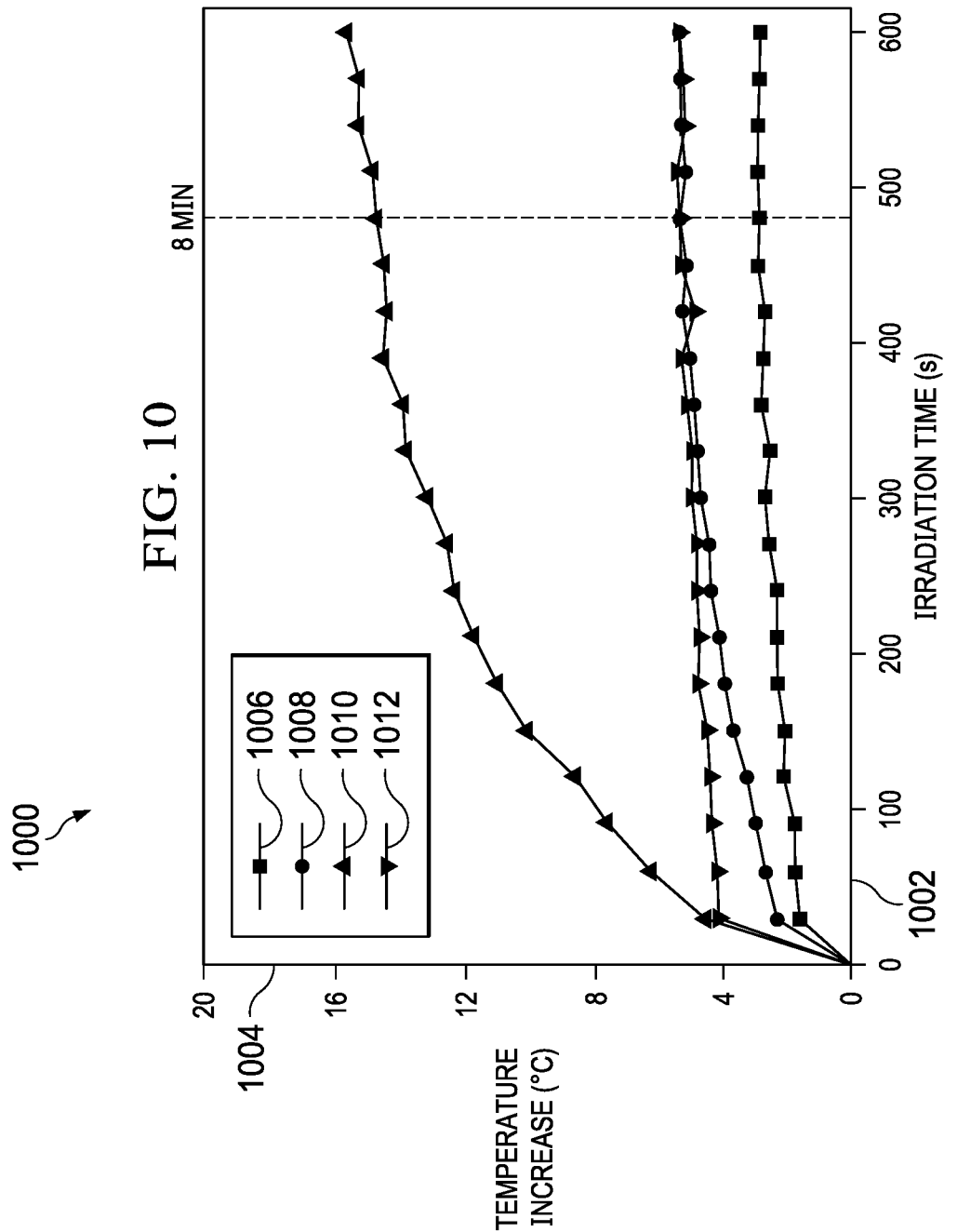
FIG. 10 is an illustration of a line graph of temperature increase versus irradiation time under the 808 nm laser irradiation from different suspensions in accordance with an illustrative embodiment.
Figure 11:
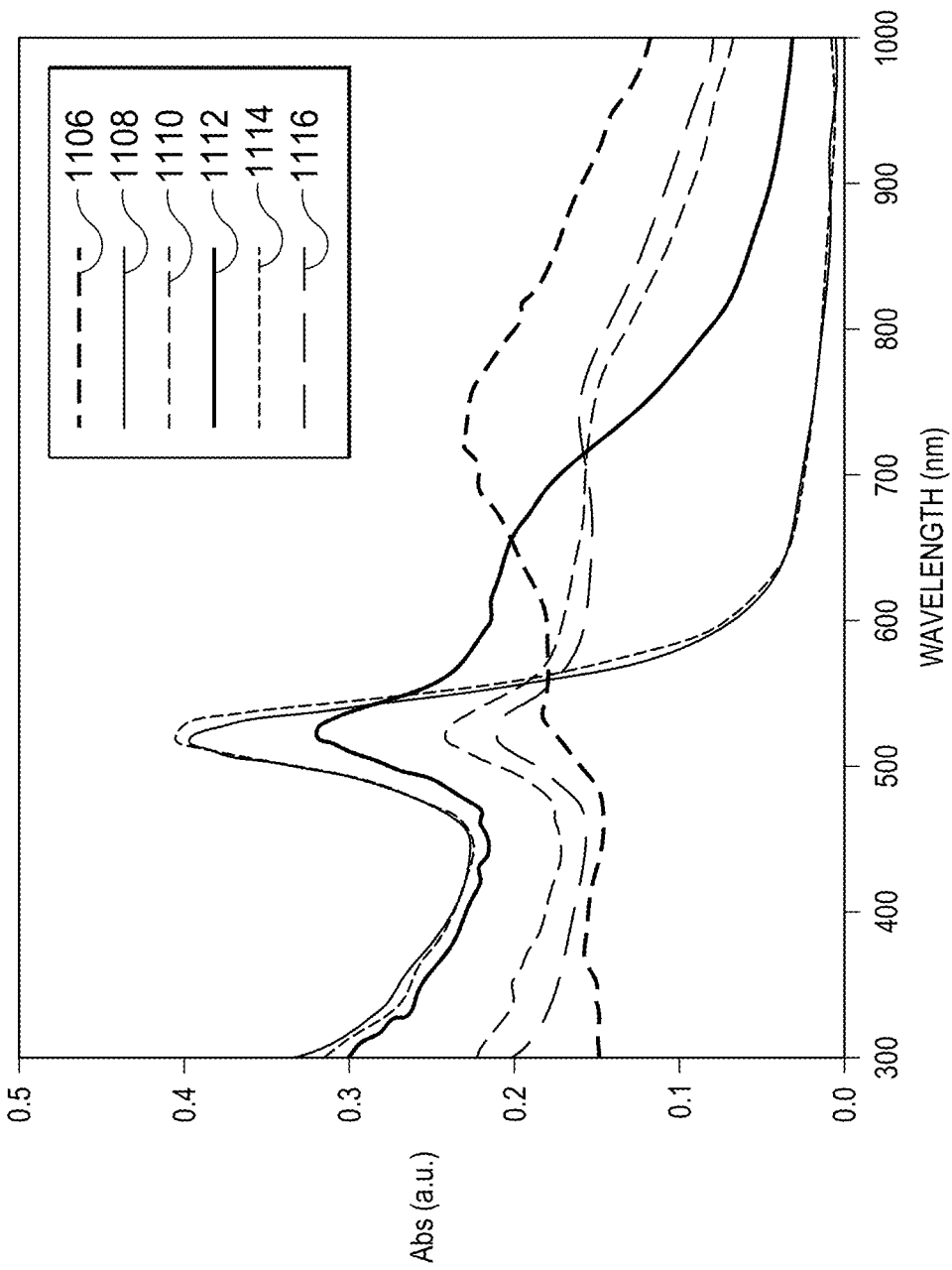
FIG. 11 is an illustration of a line graph of UV-vis spectra of suspensions having different single-stranded DNA concentrations in the gold nanoparticle aggregation-based photothermal biosensing method in accordance with an illustrative embodiment.

FIGS. 7-9 depict data collected in determining a sodium chloride concentration for a biosensor such as biosensor 104 of FIG. 1. FIG. 10 depicts data collected in determining an irradiation time for the photothermal biosensing method. FIGS. 11-13 depict data collected in determining a concentration of single-stranded DNA probes for a biosensor such as biosensor 104 of FIG. 1.

Turning now to FIG. 7, an illustration of a line graph of the UV-vis spectra of suspensions having different sodium chloride concentrations in the gold nanoparticle aggregation-induced photothermal biosensing method is depicted in accordance with an illustrative embodiment. Line graph 700 has x-axis 702 of wavelength in nanometers and y-axis 704 of absorbance in absorbance units. In line graph 700 different concentrations of sodium chloride were added to suspensions of gold nanoparticles. The concentration of sodium chloride was first optimized because of its key role in causing gold nanoparticle aggregation, resulting in a strong photothermic effect. The gold nanoparticle suspensions were characterized by UV-vis spectroscopy.

Line 706 is the absorbance data of a suspension of only the hybridization buffer. Line 706 does not have any peaks present.

Line 708 is the absorbance data of a suspension of gold nanoparticles in the hybridization buffer without sodium chloride. Line 708 has a peak at 520 nm. The peak at 520 nm is indicative of dispersed gold nanoparticles.

Line 710 is the absorbance data of a suspension of gold nanoparticles in the hybridization buffer with 20 mM sodium chloride. Line 710 has a peak at 520 nm and a shoulder peak at around 650 nm.

Line 712 is the absorbance data of a suspension of gold nanoparticles in the hybridization buffer with 40 mM sodium chloride. Line 712 has a small peak at 520 nm and a larger peak at around 750 nm. The peak at around 750 nm has appeared due to the formation of aggregates of gold nanoparticles.

Line 714 is the absorbance data of a suspension of gold nanoparticles in the hybridization buffer with 50 mM sodium chloride. Line 716 is the absorbance data of a suspension of gold nanoparticles in the hybridization buffer with 100 mM sodium chloride. Both line 714 and line 716 have peaks at around 750 nm.

As can be seen in line graph 700, with the increase of sodium chloride concentrations, along with the peak at 520 nm, a second peak at a longer wavelength around 750 nm appeared due to the formation of aggregates. The appearance of the second peak at 750 nm indicates stronger photothermal effects in the NIR range.

Viewing line graph 700, absorbance at 520 nm can be used to study the gold nanoparticles dispersed status. Viewing line graph 700, absorbance at 800 nm can be used to study the photothermal effect of aggregated gold nanoparticles in the near-infrared range. These wavelengths are viewed in greater detail in FIG. 8.

Turning now to FIG. 8, an illustration of a bar graph of absorbances at 520 and 800 nm for suspensions having different sodium chloride concentrations in the gold nanoparticle aggregation-induced photothermal biosensing method is depicted in accordance with an illustrative embodiment. Bar graph 800 has x-axis 802 of sodium chloride concentration in millimolar and y-axis 804 of absorbance in absorbance units.

Absorbances 806 at 520 nm decreased sharply moving from sodium concentration of 0 mM to sodium concentration of 40 mM owing to the depletion of dispersed gold nanoparticles. Absorbances 806 at 520 nm then reached a plateau when the sodium chloride concentration was higher than 40 mM because of the complete formation of aggregated nanoparticles. For example, absorbance measurement 810 at sodium concentration of 0 mM is approximately 0.4 absorbance units. Absorbance measurement 812 at sodium concentration of 20 mM is at approximately 0.34 absorbance units. Absorbance measurement 814 is significantly lower than absorbance measurement 812 due to depletion of dispersed gold nanoparticles. Absorbance measurement 814 is approximately 0.17 absorbance units. Each absorbance measurement for sodium concentrations of mM to 100 nM is between approximately 0.12 and 0.15 absorbance units.

Absorbances 808 at 800 nm increased moving from sodium concentration of 0 mM to sodium concentration of mM. Absorbances 808 at 800 nm reached a plateau at sodium chloride concentrations higher than 40 mM and up to a sodium chloride concentration of 100 mM. For example, absorbance measurement 816 at sodium concentration of 0 mM is approximately 0 absorbance units. Absorbance measurement 818 at sodium concentration of 20 mM is at approximately 0.05 absorbance units. Absorbance measurement 820 is significantly higher than absorbance measurement 818 due to depletion of dispersed gold nanoparticles. Absorbance measurement 820 is approximately 0.2 absorbance units. Each absorbance measurement for sodium concentrations of mM to 75 nM is between approximately 0.18 and 0.19 absorbance units.

The optical absorption changes at 800 nm displayed in absorbances 808 further proved the transformation of dispersed nanoparticles to aggregated nanoparticles when increasing the concentration of sodium chloride. The optical absorption changes at 800 nm displayed in absorbances 808 also suggested the changes from weak Photothermic effects to strong Photothermic effects.

Turning now to FIG. 9, an illustration of a bar graph of temperature increases of suspensions having different sodium chloride concentrations in the gold nanoparticle aggregation-induced photothermal biosensing method under 808 nm laser irradiation is depicted in accordance with an illustrative embodiment. Bar graph 900 has x-axis 902 of sodium chloride concentration in millimolar and y-axis 904 of temperature increase in degrees Celsius.

The changes from weak photothermic effects to strong photothermic effects due to transformation of dispersed gold nanoparticles to aggregated gold nanoparticles when increasing the concentration of sodium chloride is suggested by the results in FIGS. 7 and 8. the changes from weak photothermic effects to strong photothermic effects due to transformation of dispersed gold nanoparticles to aggregated gold nanoparticles when increasing the concentration of sodium chloride is confirmed by the data in FIG. 9.

Under the irradiation of a near-infrared laser, the temperatures of suspensions having different sodium concentrations are measured. The temperature first increased rapidly upon adding sodium chloride in the concentration range from 0 to 40 mM. Temperature change 906 for hybridization buffer is small, approximately 2.5 degrees Celsius. Temperature change 908 for gold nanoparticles in a hybridization buffer is small, approximately 5 degrees Celsius. Temperature change 910 for a suspension with a sodium chloride concentration of mM had a marked increase from both temperature change 906 and temperature change 908. Temperature change 910 for a suspension with sodium chloride concentration of 20 mM is approximately 14 degrees Celsius.

The temperature increase then reached a plateau at approximately 18 degrees Celsius in the sodium chloride concentration range of 40-65 mM, and slightly decreased afterward. The maximum temperature increase was mainly caused by increasing the aggregated gold nanoparticles formed when adding sodium chloride to bare gold nanoparticle suspensions. Upon the addition of excess sodium chloride, the aggregated gold nanoparticles further accumulated and started to precipitate, which caused lower signals in both absorbances at 800 nm in FIG. 8 and temperature measurement in FIG. 9. For example, temperature change 912 at 100 mM sodium chloride concentration is lower than temperature change 914 at 40 mM sodium chloride concentration. Precipitation of the gold nanoparticles from the suspension at greater sodium chloride concentrations causes lower temperature changes at 65 mM, 75 mM, and 100 mM concentrations of sodium chloride.

Maximum temperature change in FIG. 9 and maximum absorbance in 800 nm in FIG. 8 both occur at 40 mM sodium chloride concentration. From the data in FIGS. 8 and 9, it can be asserted that the aggregated gold nanoparticles further accumulated and started to precipitate at concentrations over 40 mM sodium chloride. The further aggregation and precipitation of the gold nanoparticles caused lower signals in both absorbances at 800 nm in FIG. 8 and temperature measurement in FIG. 9. Therefore, 40 mM of sodium chloride was selected as the concentration of sodium chloride to be used in one example of the biosensor.

FIGS. 8 and 9 are formed from data for a suspension including a saline-sodium citrate hybridization buffer and 20 nm diameter gold nanoparticles. A concentration of 40 mM of sodium chloride is selected for the biosensor having these biosensor characteristics. However, the selected sodium chloride concentration may be different for a biosensor with at least one of a different hybridization buffer, different sized gold nanoparticles, or a different concentration of gold nanoparticles. The concentration of sodium chloride in a biosensor is selected using the methods set forth above based on the absorbance and temperature increase data of different sodium chloride concentrations in the set suspension. A sodium chloride concentration is selected from a group of possible sodium chloride concentrations. The selected sodium chloride concentration is the concentration that provides a highest absorbance at 800 nm and a greatest temperature increase under irradiation without undesirably causing precipitation of the gold nanoparticles.

In some illustrative examples, a concentration of the sodium chloride is selected such that the concentration of sodium chloride is configured to produce a maximum temperature increase due to gold nanoparticle aggregation. In some illustrative examples, a concentration of the sodium chloride is selected such that the concentration of sodium chloride is configured to produce a large temperature increase due to gold nanoparticle aggregation without triggering precipitation of aggregated gold nanoparticles.

Turning now to FIG. 10, an illustration of a line graph of temperature increase versus irradiation time under the 808 nm laser irradiation from different suspensions is depicted in accordance with an illustrative embodiment. The irradiation time in the gold nanoparticle aggregation-based photothermal biosensing was also selected prior to the detection of target DNA. The irradiation time could significantly affect the measurement of readout signals. The sodium chloride concentration for suspensions utilized in the irradiation time tests is desirably the sodium chloride concentration selected based on absorbance and temperature change data, such as the data presented in FIGS. 4 and 5. The single-stranded DNA probe concentration for a suspension utilized in the irradiation time tests is desirably the single-stranded DNA probe concentration selected based on absorbance and temperature change data, such as the data presented in FIGS. 12 and 13.

Line graph 1000 is a line graph of temperature increase for some of the suspensions depicted in FIGS. 6 and 7. Line graph 1000 has x-axis 1002 of irradiation time in seconds and y-axis 1004 of temperature increase in degrees Celsius.

Line 1006 is of a suspension of only the hybridization buffer. Line 1008 is of a suspension of the hybridization buffer and gold nanoparticles. Line 1010 is of a suspension of the hybridization buffer, gold nanoparticles, and 40 mM sodium chloride. Line 1012 is of a suspension of the hybridization buffer, gold nanoparticles, 40 mM sodium chloride, and 160 nM single-stranded DNA probes. The laser power density was 5.2 W/cm$^2$.

The temperature was monitored for irradiation time in the range of 0-600 s under continuous irradiation of the 808 nm laser irradiation. Under the continuous irradiation of a near-infrared laser, the temperature of the hybridization buffer had only a slight temperature increase of approximately 2 degrees Celsius as can be seen in line 1006. Under the continuous irradiation of a near-infrared laser, the temperature of the gold nanoparticle suspension had a temperature increase of about 4 degrees Celsius, as can be seen in line 1008. Under the continuous irradiation of a near-infrared laser, the temperature of a gold nanoparticle suspension with sodium chloride and single-stranded DNA probes had a temperature increase of about 4 degrees Celsius, as can be seen in line 1012. As can be seen by comparing the gold nanoparticle suspension and a suspension of gold nanoparticles, sodium chloride, and single-stranded DNA probes.

The gold nanoparticle and sodium chloride suspension results in aggregated gold nanoparticles. The gold nanoparticle and sodium chloride suspension had a dramatic temperature increase in the first 2.5 minutes, then exhibited a stagnant increase, and finally reached the plateau of 14 degrees Celsius at approximately 8 minutes, as can be seen in line 1010. The heat balance seen in line 1010 was achieved between heat generation from the photothermal effect and heat dissipation to the environment. Therefore, to acquire a stable and sensitive temperature measurement, the laser irradiation time of 8 minutes was selected as the irradiation time for biosensing using the biosensor of the illustrative examples.

The irradiation time is selected based on the concentration of sodium chloride, concentration of single-stranded DNA probes, the laser power settings, and other biosensor characteristics. In this illustrative example, 8 minutes was selected as the set irradiation time. In other illustrative examples, a different irradiation time is selected based on when the temperature change remains substantially stable.

Turning now to FIG. 11, an illustration of a line graph of UV-vis spectra of suspensions having different single-stranded DNA concentrations in the gold nanoparticle aggregation-based photothermal biosensing method is depicted in accordance with an illustrative embodiment. Line graph 1100 is a graph of suspensions with varying concentrations of single-stranded DNA probes. Each of the suspensions in line graph 1100 includes the selected amount of sodium chloride. In this illustrative example, the selected amount of sodium chloride is 40 mM.

To obtain the best protection performance of gold nanoparticles by oligonucleotides, the concentration of single-stranded DNA probes is selectively determined. To form line graph 1100, different concentrations of single-stranded DNA probes in the range of 0-320 nM are added to gold nanoparticle suspensions, followed by the addition of 40 mM NaCl.

Line 1106 is of a suspension of the hybridization buffer, gold nanoparticles, and sodium chloride. Line 1106 displays absorbance data of suspension 509 of FIG. 5. Line 1106 includes a small peak at 520 nm and a larger peak at around 750 nm. The peak at around 750 nm has appeared due to the formation of aggregates of gold nanoparticles.

Line 1108 is of a suspension of the hybridization buffer, gold nanoparticles, sodium chloride, and 16 nM of single-stranded DNA probes. Line 1108 includes small peaks at both 520 nm and 750 nm. The peak at around 750 nm is smaller due to the protection against aggregation of the gold nanoparticles by the single-stranded DNA probes. Line 1108 has a greater peak at 520 nm than line 1106.

Line 1110 is of a suspension of the hybridization buffer, gold nanoparticles, sodium chloride, and 32 nM of single-stranded DNA probes. Line 1110 includes a peak at 520 nm and a shoulder peak at around 650 nm. Line 1110 has a greater peak at 520 nm than both line 1106 and line 1108.

Line 1112 is of a suspension of the hybridization buffer, gold nanoparticles, sodium chloride, and 80 nM of single-stranded DNA probes. Line 1112 includes a peak at 520 nm and a shoulder peak at around 650 nm. Line 1112 has a greater peak at 520 nm than each of line 1106, line 1108, and line 1110.

Line 1114 is of a suspension of the hybridization buffer, gold nanoparticles, sodium chloride, and 160 nM of single-stranded DNA probes. Line 1114 has a peak at 520 nm indicative of dispersed gold nanoparticles. Line 1114 has a greater peak at 520 nm than any of line 1106, line 1108, line 1110, and line 1112. Line 1114 does not have any other peaks.

Line 1116 is of a suspension of the hybridization buffer and gold nanoparticles. There is no sodium chloride in the suspension represented by line 1116. Line 1114 is substantially the same as line 1116, indicating that 160 nM concentration of the single-stranded DNA probes protected all of the dispersed gold nanoparticles from the sodium chloride.

In some illustrative examples, the concentration of single-stranded DNA probes in the biosensor is configured to interact with dispersed gold nanoparticles in the biosensor. In some illustrative examples, the concentration of single-stranded DNA probes in the biosensor is configured to provide an absorbance at 520 nm equivalent to an absorbance at 520 nm of a suspension of dispersed gold nanoparticles.

It can be seen from FIG. 11 that as the concentration of single-stranded DNA probes is increased in a suspension, the peak at a longer wavelength around 750 nm became weaker until it disappeared. Disappearance of the peak at 750 nm indicates reduced aggregated gold nanoparticles and better protection of the dispersed gold nanoparticles by the single-stranded DNA probes.

Turning now to FIG. 12, an illustration of a bar graph of absorbances at 520 nm and 800 nm for suspensions having different concentrations of single-stranded DNA concentrations in the gold nanoparticle aggregation-based photothermal biosensing method is depicted in accordance with an illustrative embodiment. The suspensions depicted in FIG. 12 include each of the suspensions shown in FIG. 11 as well as suspensions with greater concentrations of single-stranded DNA probes than those depicted in FIG. 11.

Absorbances 1206 at 520 nm increased gradually in the concentration range from 0 to 160 nM, implying greater quantity of dispersed gold nanoparticles due to increased single-stranded DNA probe protection. When the single-stranded DNA probe concentration was higher than 160 nM, no obvious change in UV-vis spectra was observed as compared to bare gold nanoparticles. No obvious change in absorbances 1206 when DNA probe concentration is higher than 160 nM indicates that the maximum protection of gold nanoparticles can be achieved at the single-stranded DNA probe concentration of 160 nM. Moreover, absorbance 1206 at 520 nm reached the highest value at the single-stranded DNA probe concentration of 160 nM. Absorbance value 1210 at 160 nm of single-stranded DNA probes is almost the same as absorbance value 1212 of bare gold particles. Absorbance value 1210 being almost the same as absorbance value 1212 suggests that the dispersed status of the gold nanoparticles is protected from salt-induced aggregation by the protection of ssDNA probes.

Absorbances 1208 at 800 nm decreased as the single-stranded DNA probe concentrations increased from 0 to 160 nM and reached the lowest value at 160 nM. The decrease of absorbances 1208 indicates decreased quantities of aggregated gold nanoparticles as well as weaker photothermic effects. Absorbance value 1214 at 160 nM of single-stranded DNA probes is substantially the same as absorbance value 1216 of bare gold nanoparticles.

Turning now to FIG. 13, an illustration of a bar graph of temperature increases of suspensions having different single-stranded DNA concentrations in the gold nanoparticle aggregation-based photothermal biosensing method under the 808 nm laser irradiation is depicted in accordance with an illustrative embodiment. Bar graph 1300 is a graph of temperature increases for the suspensions depicted in FIGS.

11 and 12. Bar graph 1300 has x-axis 1302 of single-stranded DNA probe concentration in nanomolar and y-axis 1304 of temperature increase in degrees Celsius.

As can be seen in bar graph 1300, under the irradiation of a near infrared laser, temperature increase 1306 of a suspension without single-stranded DNA probes is approximately 18° C. owing to the strong PT effect of gold nanoparticle aggregation. In bar graph 1300, temperature signals decrease with the increase of single-stranded DNA probe concentration. For example, temperature increase 1308 of a suspension with 16 nM of single-stranded DNA probes is lower than temperature increase 1306. Temperature signals decrease with the increase of single-stranded DNA probe concentration until reaching a plateau of approximately 6° C. temperature increase. At concentration of 160 nM single-stranded DNA probes, temperature increase 1310 is similar to temperature increase 1312 for a suspension of bare gold nanoparticles. The weaker photothermic effects of the suspensions with greater single-stranded DNA probe concentrations indicates that gold nanoparticles are protected from sodium chloride-induced aggregation by the addition of single-stranded DNA probes.

Minimum temperature change in FIG. 13 and maximum absorbance in 520 nm in FIG. 12 both occur at 160 nM single-stranded DNA probe concentration. From the data in FIGS. 12 and 13, it can be asserted that the single-stranded DNA probes do not provide any additional protection to dispersed gold nanoparticles at concentrations over 160 nM single-stranded DNA probe. From the data in FIGS. 12 and 13, it can be asserted that concentrations over 160 nM of single-stranded DNA probes would not be beneficial in the biosensor. From the data in FIGS. 12 and 13, it can be asserted that at 160 nM concentration of single-stranded DNA probes, the dispersed gold nanoparticles have substantially the same absorbances and temperature increase as bare gold nanoparticles. Therefore, 160 nM of single-stranded DNA probes was selected as the concentration of single-stranded DNA probes to be used in one example of the biosensor.

FIGS. 12 and 13 are formed from data for a suspension including a saline-sodium citrate hybridization buffer, 20 nm diameter gold nanoparticles, and 40 mM sodium chloride. A concentration of 160 nM of single-stranded DNA probes is selected for the biosensor having these biosensor characteristics. However, the selected single-stranded DNA probe concentration may be different for a biosensor with at least one of a different hybridization buffer, different sized gold nanoparticles, a different concentration of sodium chloride, or a different concentration of gold nanoparticles. The concentration of single-stranded DNA probe in a biosensor is selected using the methods set forth above based on the absorbance and temperature increase data of different single-stranded DNA probe concentrations in the set suspension. A single-stranded DNA probe is selected from a group of possible single-stranded DNA probe concentrations. The selected single-stranded DNA probe concentration is the concentration that provides a highest absorbance at 520 nm and a lowest temperature increase under irradiation without undesirably causing precipitation of the gold nanoparticles.

Figure 14:
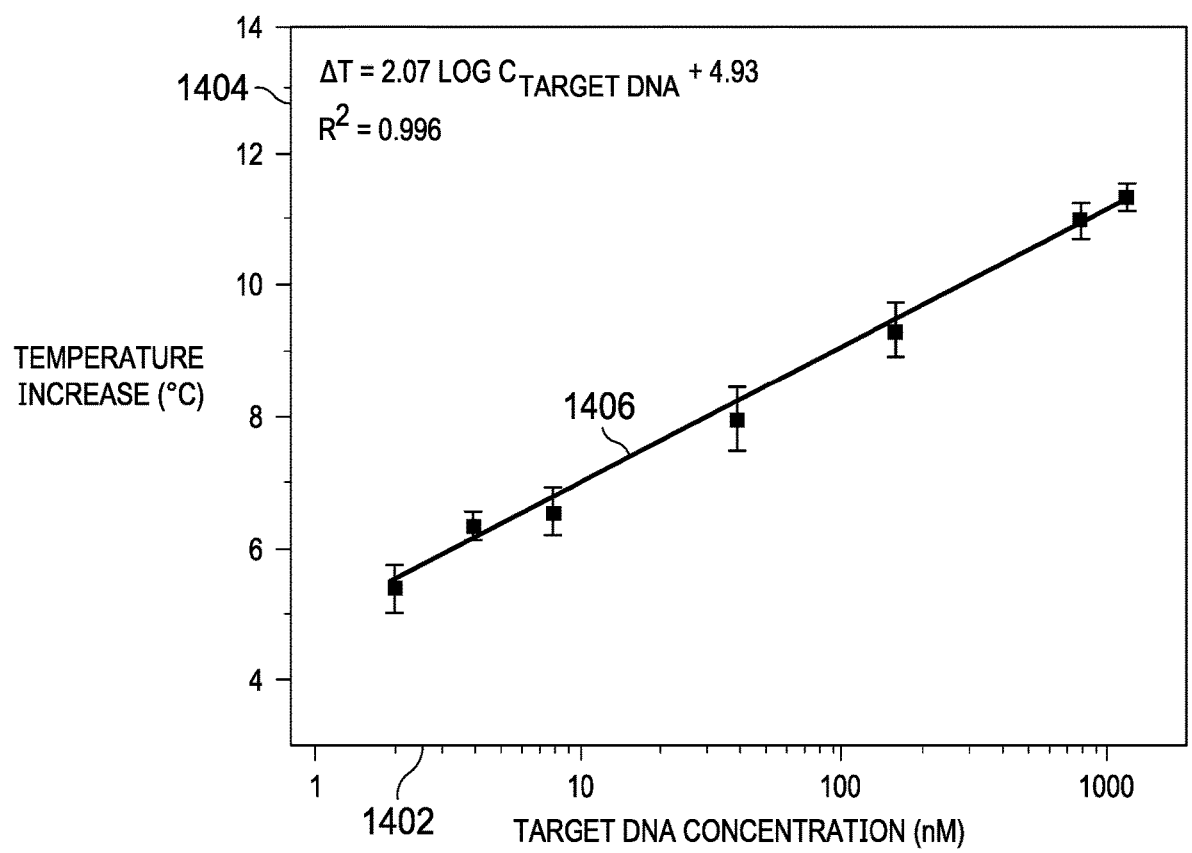
FIG. 14 is an illustration of a line graph of temperature increases vs target DNA logarithmic concentrations for *bacillus Mycobacterium tuberculosis* in accordance with an illustrative embodiment.

Turning now to FIG. 14, an illustration of a line graph of temperature increases vs target DNA logarithmic concentrations for *bacillus Mycobacterium tuberculosis* is depicted in accordance with an illustrative embodiment. Line graph 1400 is a graph of temperature increases for biosensors having varying concentrations of introduced target DNA. Line graph 1400 is formed using data from biosensors having 40 mM of sodium chloride and 160 nM of single-stranded DNA probes. Line graph 1400 has x-axis 1402 of target DNA concentration in nanomolar and y-axis 1404 of temperature increase in degrees Celsius.

Line graph 1400 is a study of target DNA-induced gold nanoparticle aggregation based photothermal biosensing platform for quantitative detection of *Mycobacterium tuberculosis* (MTB) DNA using a thermometer. Biosensors, such as biosensor 104 of FIG. 1, receive different concentrations of the target DNA. In this illustrative example, the target DNA is MTB DNA. Each biosensor with the target DNA was irradiated by a near infrared laser (808 nm) for 8 minutes at the power density of 5.2 W/cm$^2$, and the temperature was recorded using a portable digital thermometer after the irradiation.

In line graph 1400, the temperature increased with the increase of target DNA concentration. Linear relationship 1406 is obtained between the temperature increase with the logarithm of target MTB DNA concentration in the range from 2 to 1200 nM, with a squared correlation coefficient of 0.996.

The limit of detection (LOD) was calculated to be 0.28 nM based on three folds standard deviation above the blank, which was about 10-fold lower than that obtained from our colorimetric detection method, indicating high detection sensitivity of this photothermal biosensing method. Moreover, as compared to conventional colorimetric methods, the proposed photothermal biosensing platform is simple and convenient for quantitative analysis simply using an inexpensive thermometer as a signal reader, whereas conventional colorimetric methods require the use of expensive spectrometers for quantitative analysis. Furthermore, no DNA amplification was needed, and the detection could be completed within 40 minutes with no assistance from analytical instrumentation, which greatly reduced the complexity, cost, and detection time of the entire assay.

Although line graph 1400 displays data for *bacillus Mycobacterium tuberculosis*, temperature data can be collected for any biological material detected using quantitative photothermal biosensing. For example, biosensors of the illustrative examples could be used to detect any desirable nucleic acid.

The analytical performance of this photothermal biosensing platform was investigated by testing recovery in the quantitation of *M. tuberculosis* genomic DNA. The analytical recovery was evaluated by spiking different concentrations of target *M. tuberculosis* genomic DNA. Color images of different samples were captured, and temperature increases were recorded immediately after the laser irradiation.

Figure 15:
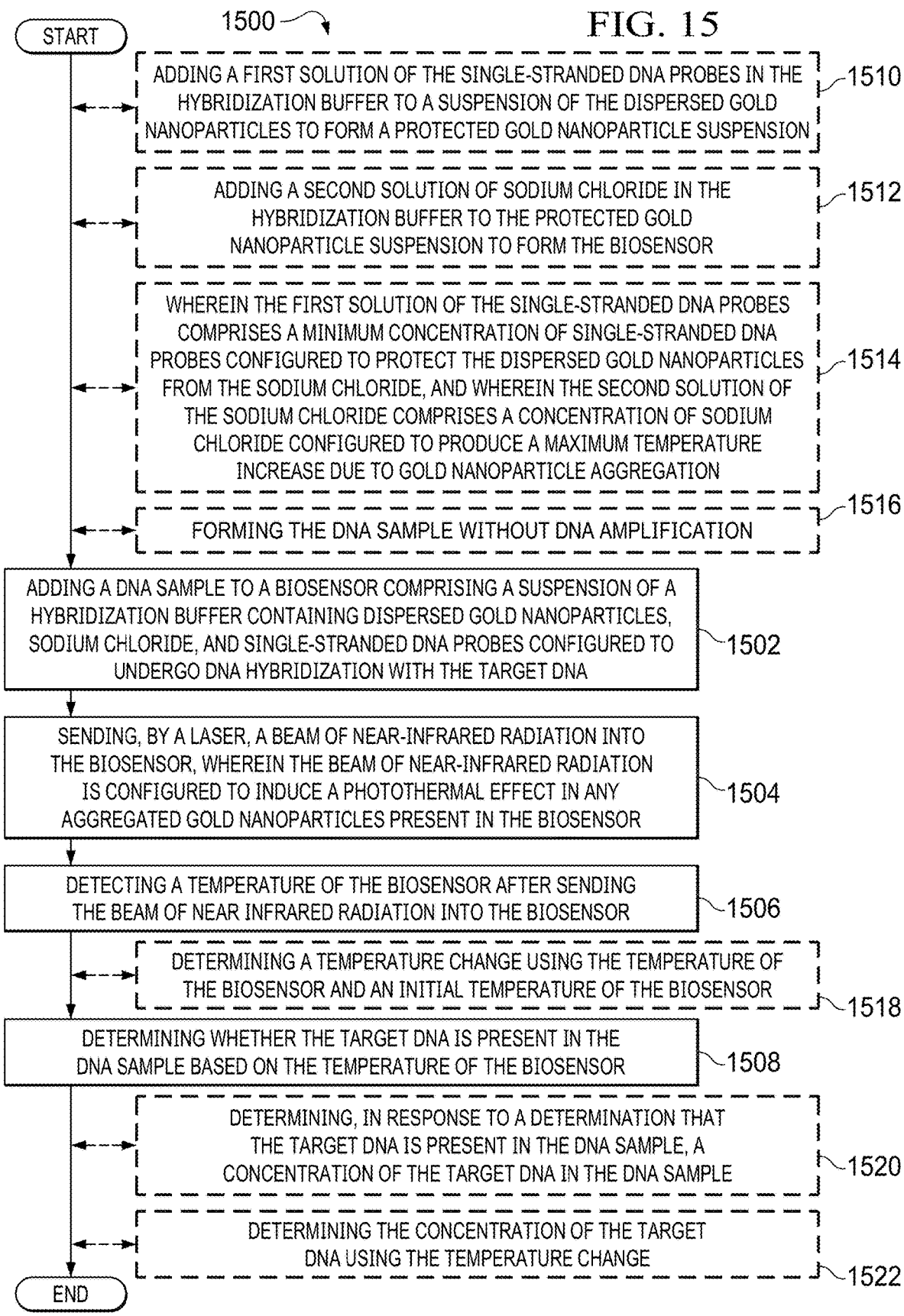
FIG. 15 is an illustration of a flowchart of a method of detecting a target DNA in accordance with an illustrative embodiment.

Turning now to FIG. 15, an illustration of a flowchart of a method of detecting a target DNA is depicted in accordance with an illustrative embodiment. Method 1500 is a method of detecting target DNA 118 of FIG. 1 using biosensor 104 of FIG. 1. Method 1500 can be performed using biosensor 201 of FIGS. 2-4. Characteristics for a biosensor to be used in method 1500 can be determined using analysis described in FIGS. 7-13. For example, a sodium chloride concentration in a biosensor utilized in method 1500 can be selected based on an analysis described in FIGS. 8 and 9. The irradiation time utilized in method 1500 can be determined according to the analysis described in FIG. 10. As another example, a single-stranded DNA probe concentration in a biosensor utilized in method 1500 can be selected based on an analysis described in FIGS. 12 and 13.

Method 1500 adds a DNA sample to a biosensor comprising a suspension of a hybridization buffer containing dispersed gold nanoparticles, sodium chloride, and single-stranded DNA probes configured to undergo DNA hybridization with the target DNA (operation 1502). Method 1500 sends, by a laser, a beam of near-infrared radiation into the biosensor, wherein the beam of near-infrared radiation is configured to induce a photothermal effect in any aggregated gold nanoparticles present in the biosensor (operation 1504). Method 1500 detects a temperature of the biosensor after sending the beam of near-infrared radiation into the biosensor (operation 1506). Method 1500 determines whether the target DNA is present in the DNA sample based on the temperature of the biosensor (operation 1508). Afterwards, method 1500 terminates.

In some illustrative examples, method 1500 determines, in response to a determination that the target DNA is present in the DNA sample, a concentration of the target DNA in the DNA sample (operation 1520).

In some illustrative examples, determining the concentration of the target DNA comprises determining a temperature change using the temperature of the biosensor and an initial temperature of the biosensor (operation 1518) and determining the concentration of the target DNA using the temperature change (operation 1522). In these illustrative examples, the concentration of the target DNA is determined by comparing the temperature change to a known relationship between target DNA concentration and temperature increase.

In some illustrative examples forming the biosensor comprises adding a first solution of the single-stranded DNA probes in the hybridization buffer to a suspension of the dispersed gold nanoparticles to form a protected gold nanoparticle suspension (operation 1510). In some illustrative examples forming the biosensor further comprises adding a second solution of sodium chloride in the hybridization buffer to the protected gold nanoparticle suspension to form the biosensor (operation 1512). In some illustrative examples, the first solution of the single-stranded DNA probes comprises a minimum concentration of single-stranded DNA probes configured to protect the dispersed gold nanoparticles from the sodium chloride, and wherein the second solution of the sodium chloride comprises a concentration of sodium chloride configured to produce a maximum temperature increase due to gold nanoparticle aggregation (operation 1514). In some illustrative examples, the second solution of the sodium chloride comprises a concentration of sodium chloride configured to produce a large temperature increase due to gold nanoparticle aggregation without triggering precipitation of aggregated gold nanoparticles.

Method 1500 is a simpler method of quantitative biosensing method. To perform method 1500, labeling of DNA probes or DNA amplification processes are not required. Method 1500 is both DNA label-free and gold nanoparticle label free. In some illustrative examples, method 1500 is described as label-free and amplification-free. In some illustrative examples, method 1500 forms the DNA sample without DNA amplification (operation 1516).

Figure 16:
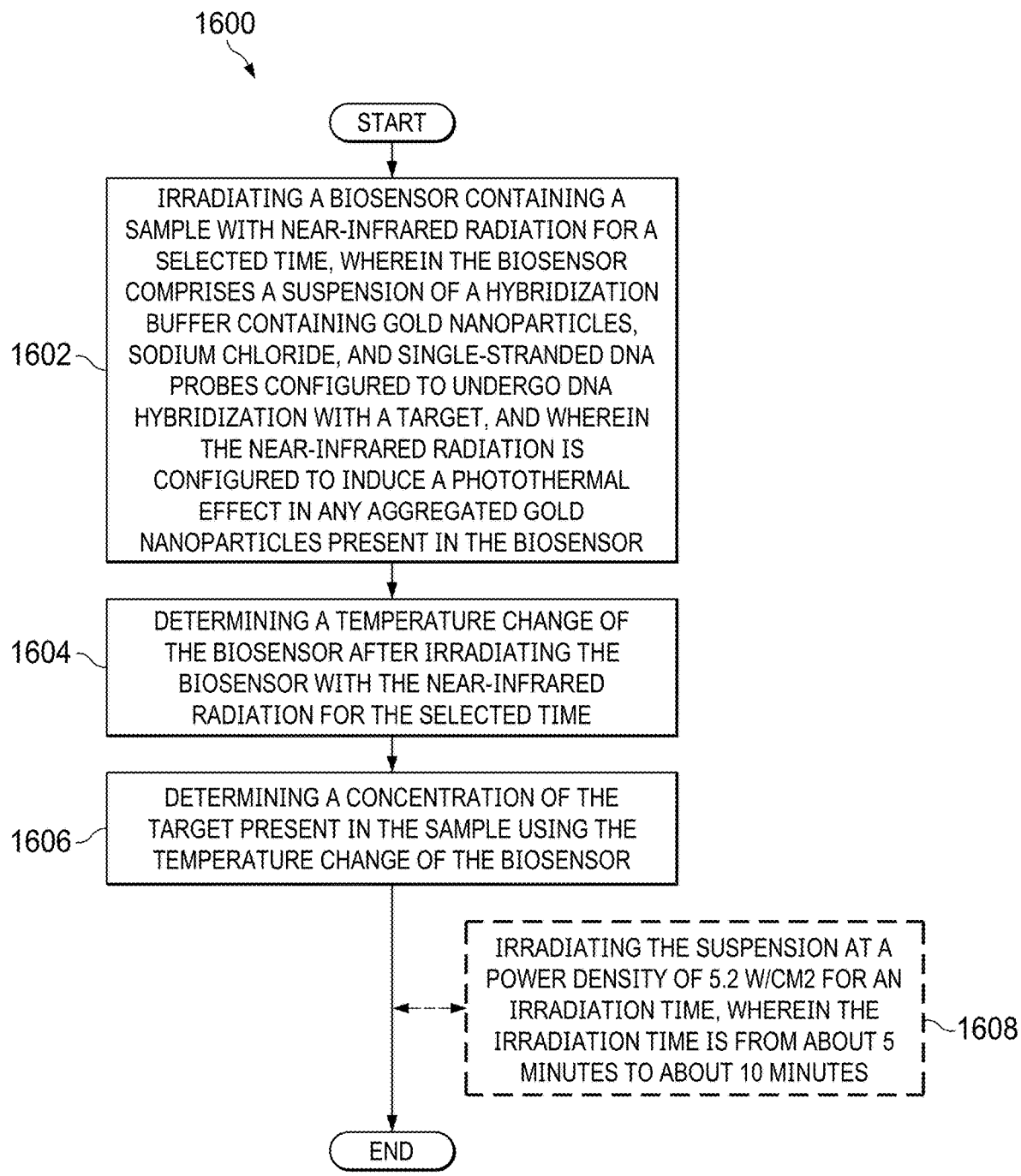
FIG. 16 is an illustration of a flowchart of a method of detecting a target DNA in accordance with an illustrative embodiment.

Turning now to FIG. 16, an illustration of a flowchart of a method of detecting a target DNA is depicted in accordance with an illustrative embodiment. Method 1600 is a method of detecting target DNA 118 of FIG. 1 using biosensor 104 of FIG. 1. Method 1600 can be performed using biosensor 201 of FIGS. 2-4. Characteristics for a biosensor to be used in method 1600 can be determined using analysis described in FIGS. 7-13. For example, a sodium chloride concentration in a biosensor utilized in method 1600 can be selected based on an analysis described in FIGS. 8 and 9. The irradiation time utilized in method 1600 can be determined according to the analysis described in FIG. 10. As another example, a single-stranded DNA probe concentration in a biosensor utilized in method 1600 can be selected based on an analysis described in FIGS. 12 and 13.

Method 1600 irradiates a biosensor containing a sample with near-infrared radiation for a selected time, wherein the biosensor comprises a suspension of a hybridization buffer containing gold nanoparticles, sodium chloride, and single-stranded DNA probes configured to undergo DNA hybridization with a target, and wherein the near-infrared radiation is configured to induce a photothermal effect in any aggregated gold nanoparticles present in the biosensor (operation 1602). Method 1600 determines a temperature change of the biosensor after irradiating the biosensor with the near-infrared radiation for the selected time (operation 1604). Method 1600 determines a concentration of the target present in the sample using the temperature change of the biosensor (operation 1606). Afterwards, method 1600 terminates.

In some illustrative examples, irradiating the biosensor further comprises irradiating the suspension at a power density of 5.2 W/cm$^2$ for an irradiation time, wherein the irradiation time is from about 5 minutes to about 10 minutes (operation 1608). In some illustrative examples, the irradiation time is selected such that the irradiation time is a first time at which heat generation from the photothermal effect and heat dissipation to the environment are substantially the same.

As used herein, the phrase "at least one of," when used with a list of items, means different combinations of one or more of the listed items may be used and only one of each item in the list may be needed. For example, "at least one of item A, item B, or item C" may include, without limitation, item A, item A and item B, or item B. This example also may include item A, item B, and item C or item B and item C. Of course, any combinations of these items may be present. In other examples, "at least one of" may be, for example, without limitation, two of item A; one of item B; and ten of item C; four of item B and seven of item C; or other suitable combinations. The item may be a particular object, thing, or a category. In other words, at least one of means any combination items and number of items may be used from the list but not all of the items in the list are required.

As used herein, "a number of," when used with reference to items means one or more items.

The flowcharts and block diagrams in the different depicted embodiments illustrate the architecture, functionality, and operation of some possible implementations of apparatuses and methods in an illustrative embodiment. In this regard, each block in the flowcharts or block diagrams may represent at least one of a module, a segment, a function, or a portion of an operation or step.

In some alternative implementations of an illustrative embodiment, the function or functions noted in the blocks may occur out of the order noted in the figures. For example, in some cases, two blocks shown in succession may be executed substantially concurrently, or the blocks may sometimes be performed in the reverse order, depending upon the functionality involved. Also, other blocks may be added in addition to the illustrated blocks in a flowchart or block diagram. Some blocks may be optional. For example, any of operation 1510 through operation 1522 may be optional. As another example, operation 1608 may be optional.

The illustrative examples provide biosensors and biosensing methods that leverage the photothermal effect of gold nanoparticles to provide quantitative genetic detection. The illustrative examples present improvements to quantitative genetic detection by providing increased sensitivity over other optical methods. The illustrative examples present improvements to quantitative genetic detection by reducing the cost of testing. The illustrative examples present improvements to quantitative genetic detection by reducing the time between collection of a DNA sample and results of testing the DNA sample. The illustrative examples present improvements to quantitative genetic detection by providing a lower cost tool for signal detection of the biosensor. Use of a thermometer, unlike conventional spectroscopy, is inexpensive and does not require sophisticated training to operate.

In the illustrative examples, unmodified gold nanoparticles are first protected by ssDNA probes from sodium chloride-induced aggregation. The unmodified gold nanoparticles are in the dispersed status and have weak PT effect under the irradiation of a near-infrared (NIR) laser. In the presence of target DNA, the protection is damaged due to DNA hybridization, which causes the aggregation of gold nanoparticles upon the addition of sodium chloride.

In the illustrative examples, the gold nanoparticle aggregation is formed and used as a photothermal agent for photothermal biosensing. An obvious temperature increase can be obtained from the aggregated gold nanoparticle suspension while being irradiated by the NIR laser. Gold nanoparticles remain in dispersed status while adding non-target DNA, which causes a negligible temperature increase due to a weak PT effect. DNA quantification can be achieved by simply recording the temperature change by using a thermometer.

The photothermic effect of different components was studied by measuring temperature changes (ATs) of different solutions after the irradiation of NIR laser for 5 minutes at a power density of 5.2 W/cm$^2$. The biosensor only had significant increase in temperature upon introduction of the target DNA.

Herein, we developed a new simple and universal method for quantitative genetic analysis using a thermometer on the basis of gold nanoparticle aggregation-induced photothermal effects. In this method, two competing processes were present between the protection and the destabilization of dispersed gold nanoparticles by single-stranded DNA (ssDNA) probes and salt (sodium chloride), respectively.

When target DNA is added to the biosensor, ssDNA probes are deprived of the surface protection of gold nanoparticles because of the hybridization, promoting gold nanoparticles to change from the dispersed status to the aggregated status. The obtained gold nanoparticle aggregation was used as a novel photothermal biosensor, correlating quantitative analysis of nucleic acids with temperature readouts, which could be simply recorded by using a common thermometer.

In the illustrative examples there is no need for DNA amplification, surface modification of gold nanoparticles, and single-stranded DNA probe modification, which greatly reduces the complexity and cost of genetic assays. The entire assay can be accomplished within 40 minutes using only a thermometer as a signal reader, without the assistance from any bulky and costly instrumentation. In addition, the unmodified gold nanoparticles can be used to adsorb various DNA probes, making it a universal platform for a broad range of genetic targets. By using *Mycobacterium tuberculosis* (MTB) DNA as a model target, high sensitivity and specificity were achieved with the limit of detection (LOD) as low as 0.28 nM, which was nearly 10-fold lower than that in the colorimetric method using a microplate reader.

The illustrative examples present a simple, low-cost, and universal gold nanoparticle aggregation-induced photothermal biosensing platform. The illustrative examples apply the gold nanoparticle aggregation-induced photothermal biosensing platform for visual quantitative genetic detection using a common thermometer. The illustrative examples exploit the photothermal effect of target-induced gold nanoparticle aggregation. By exploiting the photothermal effect of target-induced gold nanoparticle aggregation, visual quantitative biochemical analysis can be achieved by simply recording temperature signals using a common thermometer.

Compared to conventional genetic testing methods, the biosensor and biosensing methods of the illustrative examples are label- and amplification-free and can be completed in 40 minutes without the aid of any advanced analytical instruments. *Mycobacterium tuberculosis* (MTB) DNA was used as a model target to demonstrate the application of this photothermal biosensing platform. Although no costly instrument was used, high sensitivity and specificity were achieved with the limit of detection (LOD) of 0.28 nM, which was nearly lower than that of the colorimetric method using a spectrometer. This gold nanoparticle aggregation-induced photothermal biosensing strategy provides a simple, low-cost, and universal platform for broad application of visual quantitative detection of nucleic acids and many other biomolecules, particularly in point-of-care (POC) biosensing applications.

The analytical performance of this photothermal biosensing platform was investigated by testing recovery in the quantitation of *M. tuberculosis* genomic DNA. The analytical recovery was evaluated by spiking different concentrations of target *M. tuberculosis* genomic DNA. Color images of different samples were captured, and temperature increases were recorded immediately after the laser irradiation. The analytical recoveries were obtained from 94.5 to 110.2% when testing varying concentrations of the target genomic DNA spiked in SSC buffer from 13 to 39 nM (i.e., 2.5-7.5 µg/mL), which were within the acceptable recovery range for the validation of bioanalytical methods. Although genetic assays usually require cell lysis and DNA extraction before DNA hybridization under optimal hybridization conditions, this biosensing system was also challenged by directly spiking target DNA in a 50% normal human serum sample. The acceptable analytical recovery of 91.5% was acquired, even with 50% normal human serum sample, which further demonstrated the excellent performance of this method even in a complex matrix. Furthermore, as compared to color changes observed by the naked eye, the photothermal biosensing based on target-induced gold nanoparticle aggregation provided a simple yet reliable platform for the quantitative detection of nucleic acids.

We, for the first time, developed a simple yet versatile gold nanoparticle aggregation-induced photothermal biosensing platform for sensitive and quantitative detection of nucleic acids using a thermometer. The quantitation detection can be achieved by simply using a thermometer as the signal reader with no assistance from any specialized and costly analytical instrumentation. Although a low-cost thermometer was used as the signal reader, high sensitivity was achieved with the LOD as low as 0.28 nM, about 10-fold lower than the LOD in the colorimetric detection method using a spectrometer. Moreover, it is a universal platform for DNA detection, as labeling of DNA probes, gold nanoparticles, or DNA amplification processes are not required, which greatly reduces the complexity and cost of detection assays. Furthermore, this photothermal biosensing platform also provides unprecedented potential for the quantitative detection of a wide range of biochemicals and biological organisms, not solely nucleic acids. For instance, by using DNA-based aptamers, this platform can be applied to detect a variety of chemicals ranging from protein biomarkers, microorganisms, cancer cells, to metal ions (e.g., $Hg_{2+}$). Considering more and more inexpensive portable yet powerful NIR laser pointers become commercially available, this novel biosensing method will bring a new horizon to conventional detection methods particularly for point-of-care testing (POCT).

The description of the different illustrative embodiments has been presented for purposes of illustration and description, and is not intended to be exhaustive or limited to the embodiments in the form disclosed. Many modifications and variations will be apparent to those of ordinary skill in the art. Further, different illustrative embodiments may provide different features as compared to other illustrative embodiments. The embodiment or embodiments selected are chosen and described in order to best explain the principles of the embodiments, the practical application, and to enable others of ordinary skill in the art to understand the disclosure for various embodiments with various modifications as are suited to the particular use contemplated.

What is claimed is:

1. A method of detecting a target DNA, the method comprising:
   adding a DNA sample to a biosensor comprising a suspension of a hybridization buffer containing dispersed gold nanoparticles, sodium chloride, and single-stranded DNA probes configured to undergo DNA hybridization with the target DNA;
   sending, by a laser, a beam of near-infrared radiation into the biosensor, wherein the beam of near-infrared radiation is configured to induce a photothermal effect in any aggregated gold nanoparticles present in the biosensor; and
   detecting a temperature of the biosensor after sending the beam of near-infrared radiation into the biosensor;
   determining whether the target DNA is present in the DNA sample based on the temperature of the biosensor;
   adding a first solution of the single-stranded DNA probes in the hybridization buffer to a suspension of the dispersed gold nanoparticles to form a protected gold nanoparticle suspension; and
   adding a second solution of sodium chloride in the hybridization buffer to the protected gold nanoparticle suspension to form the biosensor.

2. The method of claim 1 further comprising:
   determining, in response to a determination that the target DNA is present in the DNA sample, a concentration of the target DNA in the DNA sample.

3. The method of claim 2, wherein determining the concentration of the target DNA comprises:
   determining a temperature change using the temperature of the biosensor and an initial temperature of the biosensor; and
   determining the concentration of the target DNA using the temperature change.

4. The method of claim 1, wherein the first solution of the single-stranded DNA probes comprises a minimum concentration of single-stranded DNA probes configured to protect the dispersed gold nanoparticles from the sodium chloride, and wherein the second solution of the sodium chloride comprises a concentration of sodium chloride configured to produce a maximum temperature increase due to gold nanoparticle aggregation.

5. The method of claim 1 further comprising:
   forming the DNA sample without DNA amplification.

6. A biosensing system configured to detect a target DNA, the biosensing system comprising:
   a biosensor comprising a suspension of a hybridization buffer containing dispersed gold nanoparticles, sodium chloride, and single-stranded DNA probes configured to undergo DNA hybridization with the target DNA; and
   a laser configured to direct a beam of near-infrared radiation into the biosensor, wherein the beam of near-infrared radiation is configured to induce a photothermal effect in any aggregated gold nanoparticles present in the biosensor,
   wherein the dispersed gold nanoparticles have a diameter of at least 20 nanometers.

7. The biosensing system of claim 6, wherein the biosensor is configured to operate such that the biosensor and a DNA sample to be introduced to the biosensor are label-free and DNA amplification-free.

8. The biosensing system of claim 6 further comprising:
   a thermometer configured to detect temperature changes of the suspension.

9. The biosensing system of claim 6, wherein the biosensor comprises a concentration of sodium chloride configured to produce a maximum temperature increase due to gold nanoparticle aggregation without triggering precipitation of aggregated gold nanoparticles.

10. The biosensing system of claim 9, wherein the biosensor comprises a concentration of single-stranded DNA probes configured to interact with dispersed gold nanoparticles.

11. The biosensing system of claim 9, wherein the biosensor comprises a concentration of single-stranded DNA probes configured to provide the biosensor with a temperature increase in response to a beam of near-infrared radiation equivalent to a temperature increase in response to a beam of near-infrared radiation of a suspension of dispersed gold nanoparticles.

12. The biosensing system of claim 6, wherein the laser is a near-infrared (NIR) laser having a wavelength from about 750 nm to about 850 nm.

13. A biosensing system configured to detect a target DNA, the biosensing system comprising:
   a biosensor comprising a suspension of a hybridization buffer containing dispersed gold nanoparticles, sodium chloride, and single-stranded DNA probes configured to undergo DNA hybridization with the target DNA;
   a laser configured to direct a beam of near-infrared radiation into the biosensor, wherein the beam of near-infrared radiation is configured to induce a photothermal effect in any aggregated gold nanoparticles present in the biosensor; and
   a thermometer configured to detect temperature changes of the suspension,
   wherein the biosensing system has a limit of detection of about 0.28 nM.

14. A biosensing system configured to detect a target DNA, the biosensing system comprising:
   a biosensor comprising a suspension of a hybridization buffer containing dispersed gold nanoparticles, sodium chloride, and single-stranded DNA probes configured to undergo DNA hybridization with the target DNA; and a laser configured to direct a beam of near-infrared radiation into the biosensor, wherein the beam of near-infrared radiation is configured to induce a photothermal effect in any aggregated gold nanoparticles present in the biosensor, wherein the biosensor comprises a concentration of sodium chloride configured to produce a maximum temperature increase due to gold nanoparticle aggregation without triggering precipitation of aggregated gold nanoparticles, and wherein the biosensor comprises a minimum concentration of single-stranded DNA probes configured to protect the dispersed gold nanoparticles from the sodium chloride.

15. A biosensing system configured to detect a target DNA, the biosensing system comprising:
a biosensor comprising a suspension of a hybridization buffer containing dispersed gold nanoparticles, sodium chloride, and single-stranded DNA probes configured to undergo DNA hybridization with the target DNA; and
a laser configured to direct a beam of near-infrared radiation into the biosensor, wherein the beam of near-infrared radiation is configured to induce a photothermal effect in any aggregated gold nanoparticles present in the biosensor,
wherein the biosensor comprises 40 milliMolar concentration of sodium chloride.

16. An aggregation-induced quantitative photothermal biosensing method of detecting a target, the method comprising:
irradiating a biosensor containing a sample with near-infrared radiation for a selected time, wherein the biosensor comprises a suspension of a hybridization buffer containing gold nanoparticles, sodium chloride, and single-stranded DNA probes configured to undergo DNA hybridization with a target, and wherein the near-infrared radiation is configured to induce a photothermal effect in any aggregated gold nanoparticles present in the biosensor;
determining a temperature change of the biosensor after irradiating the biosensor with the near-infrared radiation for the selected time;
determining a concentration of the target present in the sample using the temperature change of the biosensor; and
irradiating the suspension at a power density of 5.2 W/cm$^2$ for an irradiation time, wherein the irradiation time is from about 5 minutes to about 10 minutes.

17. An aggregation-induced quantitative photothermal biosensing method of detecting a target, the method comprising:
irradiating a biosensor containing a sample with near-infrared radiation for a selected time, wherein the biosensor comprises a suspension of a hybridization buffer containing gold nanoparticles, sodium chloride, and single-stranded DNA probes configured to undergo DNA hybridization with a target, and wherein the near-infrared radiation is configured to induce a photothermal effect in any aggregated gold nanoparticles present in the biosensor;
determining a temperature change of the biosensor after irradiating the biosensor with the near-infrared radiation for the selected time; and
determining a concentration of the target present in the sample using the temperature change of the biosensor,
wherein the target is a genomic DNA sequence extracted from one of *M. tuberculosis* genomic DNA, *B. pertussis, E. coli*, breast cancer cells (MCF-7), cancer associated miRNA (miRNA-141), or parasitic infection related *G. lamblia*.

* * * * *